US010377788B2

United States Patent
Aoki et al.

(10) Patent No.: US 10,377,788 B2
(45) Date of Patent: Aug. 13, 2019

(54) METHOD FOR PRODUCING GLYCOSIDE COMPOUNDS

(71) Applicant: BONAC CORPORATION, Kurume-shi, Fukuoka (JP)

(72) Inventors: Eriko Aoki, Kurume (JP); Takashi Kinoshita, Kurume (JP); Akihiro Itoh, Kurume (JP); Tadaaki Ohgi, Kurume (JP)

(73) Assignee: BONAC CORPORATION, Kurume (JP)

( * ) Notice: Subject to any disclaimer, the term of this patent is extended or adjusted under 35 U.S.C. 154(b) by 3 days.

(21) Appl. No.: 15/563,841

(22) PCT Filed: Apr. 1, 2016

(86) PCT No.: PCT/JP2016/060971
§ 371 (c)(1),
(2) Date: Oct. 2, 2017

(87) PCT Pub. No.: WO2016/159374
PCT Pub. Date: Oct. 6, 2016

(65) Prior Publication Data
US 2018/0079768 A1    Mar. 22, 2018

(30) Foreign Application Priority Data

Apr. 2, 2015  (JP) .................................. 2015-076170
Jun. 17, 2015 (JP) .................................. 2015-122009

(51) Int. Cl.
| | |
|---|---|
| *C07H 1/00* | (2006.01) |
| *C07H 1/02* | (2006.01) |
| *C07H 13/00* | (2006.01) |
| *C07H 19/06* | (2006.01) |
| *C07H 19/16* | (2006.01) |
| *C07H 23/00* | (2006.01) |
| *C08G 65/34* | (2006.01) |
| *C08G 75/02* | (2016.01) |
| *C07H 19/067* | (2006.01) |
| *C07H 19/167* | (2006.01) |

(52) U.S. Cl.
CPC .............. *C07H 13/00* (2013.01); *C07H 1/00* (2013.01); *C07H 1/02* (2013.01); *C07H 19/06* (2013.01); *C07H 19/067* (2013.01); *C07H 19/16* (2013.01); *C07H 19/167* (2013.01); *C07H 23/00* (2013.01); *C08G 65/34* (2013.01); *C08G 75/02* (2013.01)

(58) Field of Classification Search
None
See application file for complete search history.

(56) References Cited

U.S. PATENT DOCUMENTS

| | | | |
|---|---|---|---|
| 2,930,815 A * | 3/1960 | Nedwick ............... | C07C 319/18 564/501 |
| 3,933,813 A | 1/1976 | Beschke et al. | |
| 5,294,637 A | 3/1994 | Chen et al. | |
| 5,478,854 A | 12/1995 | Farina et al. | |
| 5,646,176 A | 7/1997 | Golik et al. | |
| 2001/0023255 A1 | 9/2001 | Golik et al. | |
| 2014/0206856 A1 | 7/2014 | Aoki et al. | |

FOREIGN PATENT DOCUMENTS

| | | |
|---|---|---|
| EP | 1995252 A1 | 11/2008 |
| JP | S48/080508 A | 10/1973 |
| JP | H06-080662 A | 3/1994 |
| JP | H07-149779 A | 6/1995 |
| JP | 2001-199936 A | 7/2001 |
| WO | WO 2008/090829 A1 | 7/2008 |
| WO | WO 2010/079813 A1 | 7/2010 |
| WO | WO 2013/027843 A1 | 2/2013 |

OTHER PUBLICATIONS

European Patent Office, Extended European Search Report in European Patent Application No. 16773254.4 (dated Jan. 3, 2019).
Sergeev et al., "Reaction of dithiophenols with dicarboxylic acid bisimides," *Chemical Abstracts*, 91: 6, abstract 158183a (1979).
Japanese Patent Office, International Preliminary Report on Patentability and Written Opinion of the International Searching Authority in International Patent Application No. PCT/JP2016/060971 (dated Oct. 3, 2017).
Japanese Patent Office, International Search Report in International Patent Application No. PCT/JP2016/060971 (dated Jun. 28, 2016).

* cited by examiner

*Primary Examiner* — Layla D Berry
(74) *Attorney, Agent, or Firm* — Leydig, Voit & Mayer, Ltd.

(57) ABSTRACT

The invention provides a production method of a glycoside compound or a salt thereof, which includes subjecting a thioether compound and an alcohol compound to a coupling reaction in the presence of a halogenating agent, a desiccant and a Lewis acid, and then distillation in the presence of at least one kind of additive selected from a sulfur-containing antioxidant and a maleimide group-containing compound to give a thioether compound and a step of subjecting a glycoside compound and a thioether compound to a coupling reaction in the presence of a halogenating agent, a desiccant and a Lewis acid to give a glycoside compound. By this method, a phosphoramidite preferable for the production (synthesis) of a nucleic acid can be produced more efficiently at a high purity.

20 Claims, No Drawings

METHOD FOR PRODUCING GLYCOSIDE COMPOUNDS

CROSS-REFERENCE TO RELATED APPLICATIONS

This patent application is the U.S. national phase of International Patent Application No. PCT/JP2016/060971, filed Apr. 1, 2016, which claims the benefit of Japanese Patent Application No. 2015-076170, filed on Apr. 2, 2015, and Japanese Patent Application No. 2015-122009, filed on Jun. 17, 2015, which are incorporated by reference in their entireties herein.

TECHNICAL FIELD

The present invention relates to a production method of a glycoside compound.

BACKGROUND ART

As a production (synthesis) method of nucleic acids such as DNA, RNA and the like, for example, a phosphoramidite method and the like are used. As a starting material for the nucleic acid synthesis by the phosphoramidite method, phosphoramidite of nucleoside (hereinafter to be simply referred to as "phosphoramidite") is used. Examples of the protecting group at the 2'-position of the aforementioned phosphoramidite include many protecting groups such as TBDMS (tert-butyldimethylsilyl) group, TOM (triisopropylsilyloxymethyl) group, ACE (bis(2-acetoxyethoxy) methyl) group and the like.

However, since the production cost of conventional phosphoramidites such as TOM amidite, ACE amidite and the like is high, they are not convenient as starting materials for the synthesis of pharmaceutical products and the like. In addition, the yield and purity of nucleic acid are sometimes not very high when nucleic acid is synthesized by a coupling (condensation) reaction using TBDMS amidite.

Thus, the development of a protecting group capable of providing a phosphoramidite which can be produced at a low cost and can produce a nucleic acid in a high yield with high purity has been tried (patent documents 1 and 2).

DOCUMENT LIST

Patent Documents patent document 1: WO 2013/027843
patent document 2: WO 2008/090829

SUMMARY OF THE INVENTION

Problems to be Solved by the Invention

The present invention aims to provide a method of producing, more efficiently at a high purity, a phosphoramidite preferable for the production (synthesis) of a nucleic acid.

Means of Solving the Problems

The present inventors have conducted intensive studies in an attempt to solve the aforementioned problems and found that phosphoramidite can be produced more efficiently at a high purity as compared to conventional methods by changing the selection of reagents for introduction of a protecting group, the order of addition thereof and reaction conditions thereof, as well as by studying a preparation method of a starting material (amidite reagent) (e.g., improvement of purity of amidite reagent by studying distillation method (selection of additive)), which resulted in the completion of the present invention.

Accordingly, the present invention provides the following.

[1] A method of producing a glycoside compound represented by the formula (I):

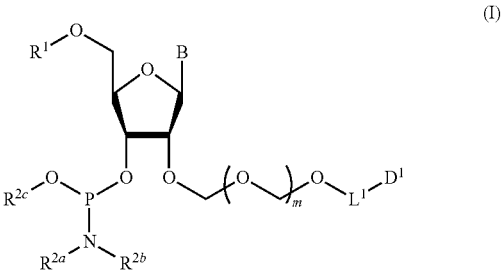

wherein $R^1$ is a hydroxyl-protecting group; $R^{2a}$ and $R^{2b}$ are the same or different and each is a hydrogen atom or a substituent; $R^{2c}$ is a hydrogen atom, an electron-withdrawing group or a substituent optionally substituted by an electron-withdrawing group; $R^{2a}$ and $R^{2b}$ optionally form a ring together with a nitrogen atom bonded thereto; B is an atomic group having a nucleic acid base skeleton; $L^1$ is an alkylene group; $D^1$ is an electron-withdrawing group; and m is a positive integer, or a salt thereof, comprising a step of subjecting a thioether compound represented by the formula (103):

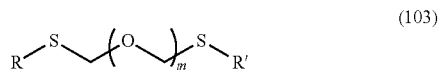

wherein m is as defined above; and R and R' are the same or different and each is an alkyl group, an alkenyl group, an alkynyl group, an aryl group, an aralkyl group, a cycloalkyl group, a cycloalkenyl group, a cycloalkylalkyl group, a cycloalkenylalkyl group or an alkoxyalkyl group, and an alcohol compound represented by the formula (105):

wherein each symbol is as defined above, to a coupling reaction in the presence of a halogenating agent, a desiccant and a Lewis acid, and then to distillation in the presence of at least one kind of additive selected from a sulfur-containing antioxidant and a maleimide group-containing compound to give a thioether compound represented by the formula (104):

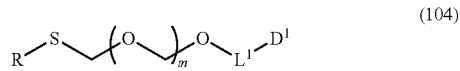

wherein each symbol is as defined above (Step 0); and a step of subjecting a glycoside compound represented by the formula (Ia):

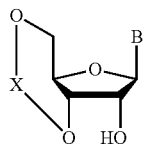
(Ia)

wherein B is as defined above; and X is a group represented by the following formula:

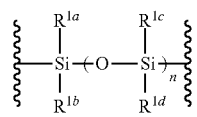

wherein n is 0 or 1; and $R^{1a}$-$R^{1d}$ are the same or different and each is a hydrogen atom, an alkyl group or an alkoxy group, and a thioether compound represented by the formula (104) to a coupling reaction in the presence of a halogenating agent, a desiccant and a Lewis acid to give a glycoside compound represented by the formula (Ib):

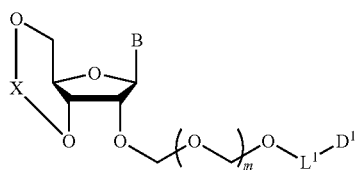
(Ib)

wherein each symbol is as defined above (Step 1).

[2] The production method of the above-mentioned [1], further comprising a step of deprotecting the compound represented by the formula (Ib) to give a glycoside compound represented by the formula (Ic):

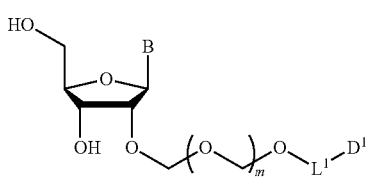
(Ic)

wherein each symbol is as defined in the above-mentioned [1](Step 2).

[3] The production method of the above-mentioned [2], further comprising a step of introducing a hydroxyl-protecting group into the glycoside compound represented by the formula (Ic) to give a glycoside compound represented by the formula (Id):

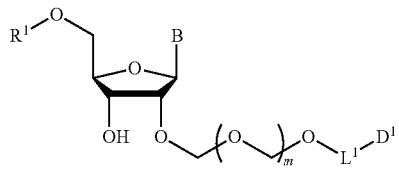
(Id)

wherein each symbol is as defined in the above-mentioned [1](Step 3).

[4] The production method of the above-mentioned [3], further comprising a step of phosphorylating the glycoside compound represented by the formula (Id) to give glycoside compound represented by the formula (I) (Step 4).

[5] A method of producing a glycoside compound represented by the formula (Ib):

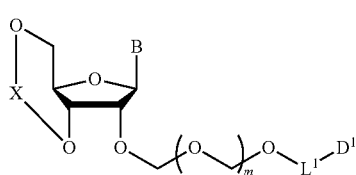
(Ib)

wherein B is an atomic group having a nucleic acid base skeleton; $L^1$ is an alkylene group; $D^1$ is an electron-withdrawing group; and m is a positive integer, comprising a step of subjecting a thioether compound represented by the formula (103):

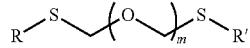
(103)

wherein m is as defined above; and R and R' are the same or different and each is an alkyl group, an alkenyl group, an alkynyl group, an aryl group, an aralkyl group, a cycloalkyl group, a cycloalkenyl group, a cycloalkylalkyl group, a cycloalkenylalkyl group or an alkoxyalkyl group, and an alcohol compound represented by the formula (105):

(105)

wherein each symbol is as defined above, to a coupling reaction in the presence of a halogenating agent, a desiccant and a Lewis acid, and then to distillation in the presence of at least one kind of additive selected from a sulfur-containing antioxidant and a maleimide group-containing compound to give a thioether compound represented by the formula (104):

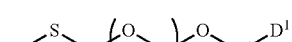
(104)

wherein each symbol is as defined above (Step 0); and a step of subjecting a glycoside compound represented by the formula (Ia):

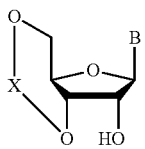
(Ia)

wherein B is as defined above; and X is a group represented by the following formula:

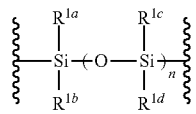

wherein n is 0 or 1; and $R^{1a}$-$R^{1d}$ are the same or different and each is a hydrogen atom, an alkyl group or an alkoxy group, and a thioether compound represented by the formula (104) to a coupling reaction in the presence of a halogenating agent, a desiccant and a Lewis acid (Step 1).

[6] A method of producing a glycoside compound represented by the formula (Ic):

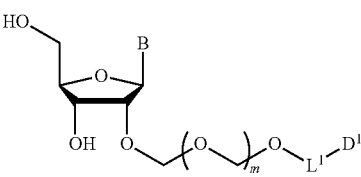
(Ic)

wherein B is an atomic group having a nucleic acid base skeleton; $L^1$ is an alkylene group; $D^1$ is an electron-withdrawing group; and m is a positive integer, comprising a step of subjecting a thioether compound represented by the formula (103):

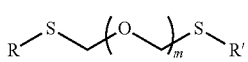
(103)

wherein m is as defined above; and R and R' are the same or different and each is an alkyl group, an alkenyl group, an alkynyl group, an aryl group, an aralkyl group, a cycloalkyl group, a cycloalkenyl group, a cycloalkylalkyl group, a cycloalkenylalkyl group or an alkoxyalkyl group, and an alcohol compound represented by the formula (105):

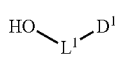
(105)

wherein each symbol is as defined above, to a coupling reaction in the presence of a halogenating agent, a desiccant and a Lewis acid, and then to distillation in the presence of at least one kind of additive selected from a sulfur-containing antioxidant and a maleimide group-containing compound to give a thioether compound represented by the formula (104):

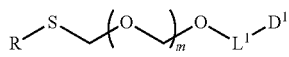
(104)

wherein each symbol is as defined above (Step 0); and a step of subjecting a glycoside compound represented by the formula (Ia):

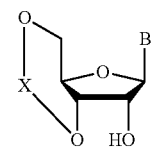
(Ia)

wherein B is as defined above; and X is a group represented by the following formula:

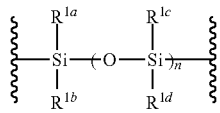

wherein n is 0 or 1; and $R^{1a}$-$R^{1d}$ are the same or different and each is a hydrogen atom, an alkyl group or an alkoxy group, and a thioether compound represented by the formula (104) to a coupling reaction in the presence of a halogenating agent, a desiccant and a Lewis acid to give a glycoside compound represented by the formula (Ib):

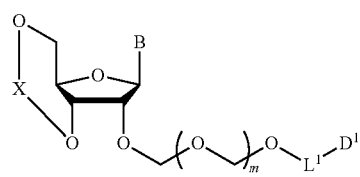
(Ib)

wherein each symbol is as defined above (Step 1); and a step of deprotecting the glycoside compound represented by the formula (Ib) (Step 2).

[7] A method of producing a glycoside compound represented by the formula (Id):

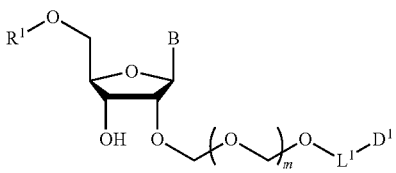
(Id)

wherein $R^1$ is a hydroxyl-protecting group; B is an atomic group having a nucleic acid base skeleton; $L^1$ is an alkylene group; $D^1$ is an electron-withdrawing group; and m is a positive integer, comprising a step of subjecting a thioether compound represented by the formula (103):

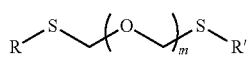
(103)

wherein m is as defined above; and R and R' are the same or different and each is an alkyl group, an alkenyl group, an alkynyl group, an aryl group, an aralkyl group, a cycloalkyl group, a cycloalkenyl group, a cycloalkylalkyl group, a cycloalkenylalkyl group or an alkoxyalkyl group, and an alcohol compound represented by the formula (105):

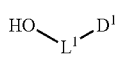
(105)

wherein each symbol is as defined above, to a coupling reaction in the presence of a halogenating agent, a desiccant and a Lewis acid, and then to distillation in the presence of at least one kind of additive selected from a sulfur-containing antioxidant and a maleimide group-containing compound to give a thioether compound represented by the formula (104):

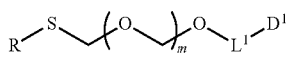
(104)

wherein each symbol is as defined above (Step 0); and a step of subjecting a glycoside compound represented by the formula (Ia):

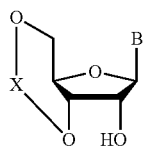
(Ia)

wherein B is as defined above; and X is a group represented by the following formula:

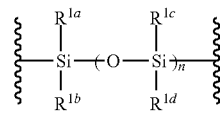

wherein n is 0 or 1; and $R^{1a}$-$R^{1d}$ are the same or different and each is a hydrogen atom, an alkyl group or an alkoxy group, and a thioether compound represented by the formula (104) to a coupling reaction in the presence of a halogenating agent, a desiccant and a Lewis acid to give a glycoside compound represented by the formula (Ib):

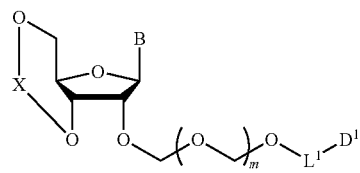
(Ib)

wherein each symbol is as defined above (Step 1); a step of deprotecting the glycoside compound represented by the formula (Ib) to give a glycoside compound represented by the formula (Ic):

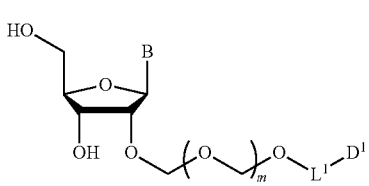
(Ic)

wherein each symbol is as defined above (Step 2); and a step of introducing a hydroxyl-protecting group into the glycoside compound represented by the formula (Ic) (Step 3).

[8] A method of producing a glycoside compound represented by the formula (I):

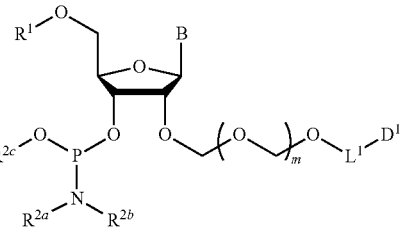
(I)

wherein $R^1$ is a hydroxyl-protecting group; $R^{2a}$ and $R^{2b}$ are the same or different and each is a hydrogen atom or a substituent; $R^{2c}$ is a hydrogen atom, an electron-withdrawing group or a substituent optionally substituted by an electron-withdrawing group; $R^{2a}$ and $R^{2b}$ optionally form a ring together with a nitrogen atom bonded thereto; B is an atomic group having a nucleic acid base skeleton; $L^1$ is an alkylene group; $D^1$ is an electron-withdrawing group; and m is a positive integer, comprising a step of subjecting a thioether compound represented by the formula (103):

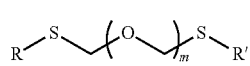
(103)

wherein m is as defined above; and R and R' are the same or different and each is an alkyl group, an alkenyl group, an alkynyl group, an aryl group, an aralkyl group, a cycloalkyl group, a cycloalkenyl group, a cycloalkylalkyl group, a cycloalkenylalkyl group or an alkoxyalkyl group, and an alcohol compound represented by the formula (105):

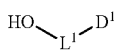
(105)

wherein each symbol is as defined above, to a coupling reaction in the presence of a halogenating agent, a desiccant and a Lewis acid, and then to distillation in the presence of at least one kind of additive selected from a sulfur-containing antioxidant and a maleimide group-containing compound to give a thioether compound represented by the formula (104):

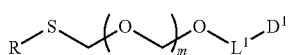
(104)

wherein each symbol is as defined above (Step 0); and a step of subjecting a glycoside compound represented by the formula (Ia):

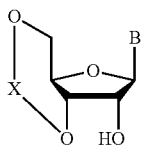
(Ia)

wherein B is as defined above; and X is a group represented by the following formula:

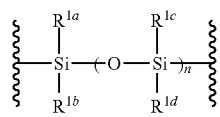

wherein n is 0 or 1; and $R^{1a}$-$R^{1d}$ are the same or different and each is a hydrogen atom, an alkyl group or an alkoxy group, and a thioether compound represented by the formula (104) to a coupling reaction in the presence of a halogenating agent, a desiccant and a Lewis acid to give a glycoside compound represented by the formula (Ib):

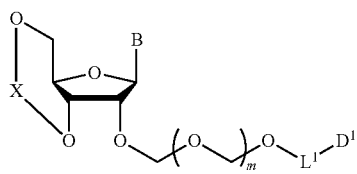
(Ib)

wherein each symbol is as defined above (Step 1); a step of deprotecting the compound represented by the formula (Ib) to give a glycoside compound represented by the formula (Ic):

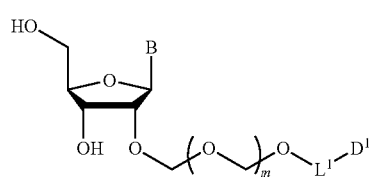
(Ic)

wherein each symbol is as defined above (Step 2); a step of introducing a hydroxyl-protecting group into the glycoside compound represented by the formula (Ic) to give a glycoside compound represented by the formula (Id):

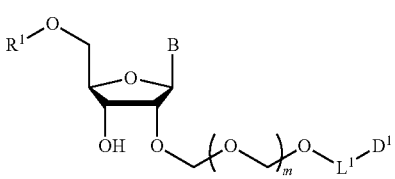
(Id)

wherein each symbol is as defined above (Step 3); and a step of phosphorylating the glycoside compound represented by the formula (Id) (Step 4).

[9] The method of any of the above-mentioned [1]-[8], wherein the additive in the distillation in Step 0 is 4,4'-bismaleimidodiphenylmethane.

[10] The method of any of the above-mentioned [1]-[9], wherein n is 1.

[11] The method of any of the above-mentioned [1]-[10], wherein $R^{1a}$-$R^{1d}$ are isopropyl groups.

[12] The method of any of the above-mentioned [1]-[11], wherein m is 1.

[13] The method of any of the above-mentioned [1]-[12], wherein $L^1$ is an ethylene group.

[14] The method of any of the above-mentioned [1]-[13], wherein $D^1$ is a cyano group.

[15] The method of any of the above-mentioned [1]-[13], wherein the thioether compound represented by the formula (104) is added after the addition of the halogenating agent, the desiccant and the Lewis acid in Step 1.

[16] The method of any of the above-mentioned [1]-[14], wherein the halogenating agent is added after the addition of the desiccant, the Lewis acid and the thioether compound represented by the formula (104) in Step 1.

[17] The method of the above-mentioned [15], wherein the Lewis acid is added after the addition of the halogenating agent in Step 1.

[18] The method of the above-mentioned [16], wherein the thioether compound represented by the formula (104) is added after the addition of the Lewis acid in Step 1.

[19] The method of any of the above-mentioned [1]-[18], wherein the halogenating agent in Step 1 is an iodinating agent.

[20] The method of the above-mentioned [19], wherein the iodinating agent is 1,3-diiodo-5,5-dimethylhydantoin or iodine.

[21] The method of any of the above-mentioned [1]-[20], wherein the desiccant is a molecular sieve.

[22] The method of any of the above-mentioned [1]-[21], wherein the Lewis acid in Step 1 is trifluoromethanesulfonic acid.

[23] The method of any of the above-mentioned [1]-[21], wherein the Lewis acid in Step 1 is methanesulfonic acid.

Effect of the Invention

According to the present invention, phosphoramidite can be produced more efficiently at a high purity.

DESCRIPTION OF EMBODIMENTS

The terms and symbols used in the following present invention are defined.

The "atomic group having a nucleic acid base skeleton" means a functional group having a nucleic acid base skeleton in the whole or a part of the structure. The "nucleic acid base skeleton" here may be a natural nucleic acid base skeleton or an artificial nucleic acid base skeleton, and preferably a natural nucleic acid base skeleton.

The natural nucleic acid base is more preferably adenine, cytosine, guanine, uracil, thymine or other nitrogen-containing aromatic ring (e.g., 5-alkylpyrimidine, 5-halogenopyrimidine, deazapurine, deazapyrimidine, azapurine, azapyrimidine).

The "halogen" is, for example, a fluorine atom, a chlorine atom, a bromine atom or an iodine atom.

The "alkyl group" means a straight chain or branched chain alkyl group having 1-30, preferably 1-12, more preferably 1-6, particularly preferably 1-4, carbon atoms, and specifically includes methyl, ethyl, n-propyl, isopropyl, n-butyl, isobutyl, sec-butyl and tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl and the like. Preferred are, for example, methyl, ethyl, n-propyl, isopropyl, n-butyl, isobutyl, sec-butyl, tert-butyl, n-pentyl, isopentyl, neopentyl, n-hexyl, isohexyl and the like.

The "alkenyl group" means a straight chain or branched chain alkenyl group having 2-30, preferably 2-12, more preferably 2-8, carbon atoms, and the aforementioned alkyl group having one or plural double bonds and the like can be mentioned. Specifically, vinyl, 1-propenyl, 2-propenyl, 1-butenyl, 2-butenyl, 3-butenyl, 1,3-butadienyl, 3-methyl-2-butenyl and the like can be mentioned.

The "alkynyl group" means a straight chain or branched chain alkynyl group having 2-30, preferably 2-12, more preferably 2-8, carbon atoms, and the aforementioned alkyl group having one or plural triple bonds and the like can be mentioned. Specifically, ethynyl, propynyl, propargyl, butynyl, pentynyl, hexynyl and the like can be mentioned. The alkynyl group optionally further has one or plural double bonds.

The "alkoxy group" means a straight chain or branched chain alkoxy group having 1-30, preferably 1-12, more preferably 1-6, particularly preferably 1-4, carbon atoms, and specifically, methoxy, ethoxy, n-propoxy, isopropoxy, n-butoxy, isobutoxy, sec-butoxy, tert-butoxy, n-pentyloxy, isopentyloxy, tert-pentyloxy, neopentyloxy, 2-pentyloxy, 3-pentyloxy, n-hexyloxy, 2-hexyloxy and the like can be mentioned.

The "aryl group" means an aryl group having 6-24, preferably 6-10, carbon atoms, and monocyclic aromatic hydrocarbon groups such as phenyl and the like, and polycyclic aromatic hydrocarbon groups such as 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl and the like can be mentioned.

The "aralkyl group" means an aralkyl group having 7-30, preferably 7-11, carbon atoms, and specifically, benzyl, 2-phenethyl, and naphthalenylmethyl and the like can be mentioned.

The "cycloalkyl group" means a cycloalkyl group having 3-24, preferably 3-15, carbon atoms, and specifically, cyclopropyl, cyclobutyl, cyclopentyl, cyclohexyl, cycloheptyl, cyclooctyl, bridged cyclic hydrocarbon group, spirohydrocarbon group and the like can be mentioned, and preferably, cyclopropyl, cyclobutyl, cyclopentyl, cyclohexyl, bridged cyclic hydrocarbon group and the like can be mentioned. Examples of the "bridged cyclic hydrocarbon group" include bicyclo[2.1.0]pentyl, bicyclo[2.2.1]heptyl, bicyclo[2.2.2]octyl, bicyclo[3.2.1]octyl, tricyclo[2.2.1.0]heptyl, bicyclo[3.3.1]nonane, 1-adamantyl, 2-adamantyl and the like. Examples of the "spirohydrocarbon group" include spiro[3.4]octyl and the like.

The "cycloalkenyl group" means a cycloalkenyl group having 3-24, preferably 3-7, carbon atoms containing at least one, preferably 1 or 2, double bonds, and specifically, cyclopropenyl, cyclobutenyl, cyclopentenyl, cyclohexenyl, cycloheptenyl and the like can be mentioned. The aforementioned cycloalkenyl group also includes a bridged cyclic hydrocarbon group and a spirohydrocarbon group, each having an unsaturated bond in the ring. Examples of the "bridged cyclic hydrocarbon group having an unsaturated bond in the ring" include bicyclo[2.2.2]octenyl, bicyclo[3.2.1]octenyl, tricyclo[2.2.1.0]heptenyl and the like. Examples of the "spirohydrocarbon group having an unsaturated bond in the ring" include spiro[3.4]octenyl and the like.

The "cycloalkylalkyl group" means an alkyl group (mentioned above) substituted by the aforementioned cycloalkyl group, preferably a cycloalkylalkyl group having 4-30, more preferably 4-11, carbon atoms. Specifically, cyclopropylmethyl, 2-cyclobutylethyl, cyclopentylmethyl, 3-cyclopentylpropyl, cyclohexylmethyl, 2-cyclohexylethyl, cycloheptylmethyl and the like can be mentioned.

The "alkoxyalkyl group" means an alkyl group (mentioned above) substituted by the aforementioned alkoxy group, preferably a straight chain or branched chain alkoxyalkyl group having 2-30, more preferably 2-12, carbon atoms. Specifically, methoxymethyl, methoxyethyl, ethoxymethyl, ethoxyethyl and t-butoxy methyl and the like can be mentioned.

The "alkylene group" means a straight chain or branched chain alkylene group having 1-30, preferably 1-12, more preferably 1-6, particularly preferably 1-4, carbon atoms, and specifically, methylene, ethylene, and propylene and the like can be mentioned.

Examples of the "heteroaryl group" include a monocyclic aromatic heterocyclic group and a fused aromatic heterocyclic group. Examples of the aforementioned heteroaryl include furyl (e.g., 2-furyl, 3-furyl), thienyl (e.g., 2-thienyl, 3-thienyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1,2,4-triazol-1-yl, 1,2,4-triazol-3-yl, 1,2,4-triazol-4-yl), tetrazolyl (e.g., 1-tetrazolyl, 2-tetrazolyl, 5-tetrazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), thiadiazolyl, isothiazolyl (e.g., 3-isothiazolyl, 4-isothiazolyl, 5-isothiazolyl), pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), furazanyl (e.g., 3-furazanyl), pyrazinyl (e.g., 2-pyrazinyl), oxadiazolyl (e.g., 1,3,4-oxadiazol-2-yl), benzofuryl (e.g., 2-benzo[b]furyl, 3-benzo[b]furyl, 4-benzo[b]furyl, 5-benzo[b]furyl, 6-benzo[b]furyl, 7-benzo[b]furyl), benzothienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyl (e.g., 1-benzimidazolyl, 2-benzimidazolyl, 4-benzimidazolyl, 5-benzimidazolyl), dibenzofuryl, benzoxazolyl, benzothiazolyl, quinoxalinyl (e.g., 2-quinoxalinyl, 5-quinoxalinyl, 6-quinoxalinyl), cinnolinyl (e.g., 3-cinnolinyl, 4-cinnolinyl, 5-cinnolinyl, 6-cinnolinyl, 7-cinnolinyl, 8-cinnolinyl), quinazolinyl (e.g., 2-quinazolinyl, 4-quinazolinyl, 5-quinazolinyl, 6-quinazolinyl, 7-quinazolinyl, 8-quinazolinyl), quinolyl (e.g., 2-quinolyl, 3-quinolyl, 4-quinolyl, 5-quinolyl, 6-quinolyl, 7-quinolyl, 8-quinolyl), phthalazinyl (e.g., 1-phthalazinyl, 5-phthalazinyl, 6-phthalazinyl), isoquinolyl (e.g., 1-isoquinolyl, 3-isoquinolyl, 4-isoquinolyl, 5-isoquinolyl, 6-isoquinolyl, 7-isoquinolyl, 8-isoquinolyl), puryl, pteridinyl (e.g., 2-pteridinyl, 4-pteridinyl, 6-pteridinyl, 7-pteridinyl), carbazolyl, phenanthridinyl, acridinyl (e.g., 1-acridinyl, 2-acridinyl, 3-acridinyl, 4-acridinyl, 9-acridinyl), indolyl (e.g., 1-indolyl, 2-indolyl, 3-indolyl, 4-indolyl, 5-indolyl, 6-indolyl, 7-indolyl), isoindolyl, phenazinyl (e.g., 1-phenazinyl, 2-phenazinyl) or phenothiazinyl (e.g., 1-phenothiazinyl, 2-phenothiazinyl, 3-phenothiazinyl, 4-phenothiazinyl) and the like.

The "electron-withdrawing group" is a group which easily attracts an electron from the bonded atom side as compared to a hydrogen atom. Specifically, cyano, nitro, alkylsulfonyl (e.g., methylsulfonyl, ethylsulfonyl), halogen (fluorine atom, chlorine atom, bromine atom or iodine atom), arylsulfonyl (e.g., phenylsulfonyl, naphthylsulfonyl), trihalomethyl (e.g., trichloromethyl, trifluoromethyl) and the like can be mentioned.

The "hydroxyl-protecting group" means a general hydroxyl-protecting group known to those of ordinary skill in the art, which is introduced to prevent a reaction of the hydroxyl group. For example, the protecting groups described in Protective Groups in Organic Synthesis, published by John Wiley and Sons (1980) and the like, specifically, acyl-type protecting groups such as acetyl, benzoyl and the like, alkyl-type protecting groups such as trityl, 4-methoxytrityl, 4,4'-dimethoxytrityl, benzyl and the like, silyl-type protecting group such as trimethylsilyl, tert-butyldimethylsilyl, tert-butyldiphenylsilyl and the like can be mentioned.

In the present invention, examples of the "substituent" include
(1) halogen (fluorine atom, chlorine atom, bromine atom or iodine atom);
(2) alkyl group (mentioned above);
(3) alkenyl group (mentioned above);
(4) alkynyl group (mentioned above);
(5) haloalkyl group (e.g., chloromethyl, fluoromethyl, dichloromethyl, difluoromethyl, dichlorofluoromethyl, trifluoromethyl, pentafluoroethyl etc.);
(6) aryl group (mentioned above);
(7) heteroaryl group (mentioned above);
(8) aralkyl group (mentioned above);
(9) cycloalkyl group (mentioned above);
(10) cycloalkenyl group (mentioned above);
(11) cycloalkylalkyl group (mentioned above);
(12) cycloalkenylalkyl group (e.g., cyclopentenylethyl, cyclohexenylbutyl etc.);
(13) hydroxyalkyl group (e.g., hydroxymethyl, hydroxyethyl, hydroxypropyl, hydroxybutyl etc.);
(14) alkoxyalkyl group (mentioned above);
(15) aminoalkyl group (e.g., aminomethyl, aminoethyl, aminopropyl etc.);
(16) heterocyclyl group (e.g., 1-pyrrolinyl, 2-pyrrolinyl, 3-pyrrolinyl, 1-pyrrolidinyl, 2-pyrrolidinyl, 3-pyrrolidinyl, pyrrolidinone, 1-imidazolinyl, 2-imidazolinyl, 4-imidazolinyl, 1-imidazolidinyl, 2-imidazolidinyl, 4-imidazolidinyl, imidazolidinone, 1-pyrazolinyl, 3-pyrazolinyl, 4-pyrazolinyl, 1-pyrazolidinyl, 3-pyrazolidinyl, 4-pyrazolidinyl, piperidinone, piperidino, 2-piperidinyl, 3-piperidinyl, 4-piperidinyl, 1-piperazinyl, 2-piperazinyl, piperazinone, 2-morpholinyl, 3-morpholinyl, morpholino, tetrahydropyranyl, tetrahydrofuranyl or the like);
(17) heterocyclylalkenyl group (e.g., 2-piperidinylethenyl etc.);
(18) heterocyclylalkyl group (e.g., piperidinylmethyl, piperazinylmethyl etc.);
(19) heteroarylalkyl group (e.g., pyridylmethyl, quinolin-3-ylmethyl etc.);
(20) silyl group;
(21) silyloxyalkyl group (e.g., silyloxymethyl, silyloxyethyl etc.);
(22) mono-, di- or tri-alkylsilyl group (e.g., methylsilyl, ethylsilyl etc.);
(23) mono-, di- or tri-alkylsilyloxyalkyl group (e.g., trimethylsilyloxymethyl etc.)

and the like. Each of these substituents may or may not be further substituted by an electron-withdrawing group (mentioned above).

The present invention provides a production method of the glycoside compound represented by the formula (I) (hereinafter to be also referred to as glycoside compound (I)) or a salt thereof (hereinafter to be also referred to as the production method of the present invention).

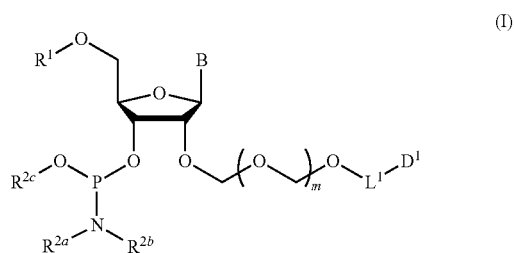

(I)

wherein B is an atomic group having a nucleic acid base skeleton; m is a positive integer; $L^1$ is an alkylene group; $D^1$ is an electron-withdrawing group; $R^1$ is a hydroxyl-protecting group; $R^{2a}$ and $R^{2b}$ are the same or different and each is a hydrogen atom or a substituent; $R^{2c}$ is a hydrogen atom, an electron-withdrawing group or a substituent optionally substituted by an electron-withdrawing group; and $R^{2a}$ and $R^{2b}$ optionally form a ring together with a nitrogen atom bonded thereto]

The production method of the present invention includes the following step (Step 1).

[Step 1]

A step of obtaining a glycoside compound represented by the formula (Ib):

(Ib)

wherein B is an atomic group having a nucleic acid base skeleton; $L^1$ is an alkylene group; $D^1$ is an electron-withdrawing group; and m is a positive integer (hereinafter to be also referred to as glycoside compound (Ib)), comprising subjecting a glycoside compound represented by the formula (Ia):

(Ia)

wherein B is as defined above, and X is a group represented by the following formula:

wherein n is 0 or 1; and $R^{1a}$-$R^{1d}$ are the same or different and each is a hydrogen atom, an alkyl group or an alkoxy group (hereinafter to be also referred to as glycoside compound (Ia)) and a thioether compound represented by the formula (104):

(104)

wherein m is as defined above; R is an alkyl group, an alkenyl group, an alkynyl group, an aryl group, an aralkyl group, a cycloalkyl group, a cycloalkenyl group, a cycloalkylalkyl group, a cycloalkenylalkyl group or an alkoxyalkyl group; $L^1$ is an alkylene group; and $D^1$ is an electron-withdrawing group) (hereinafter to be also referred to as thioether compound (104)) to a coupling reaction in the presence of a halogenating agent, a desiccant and a Lewis acid.

Therefore, the present invention also provides a production method of glycoside compound (Ib) by Step 1.

Here, thioether compound (104) is prepared by the following step (Step 0).

[Step 0]

A step of obtaining a thioether compound (104), comprising subjecting a thioether compound represented by the formula (103):

(103)

wherein m is a positive integer; and R and R' are the same or different and each is an alkyl group, an alkenyl group, an alkynyl group, an aryl group, an aralkyl group, a cycloalkyl group, a cycloalkenyl group, a cycloalkylalkyl group, a cycloalkenylalkyl group or an alkoxyalkyl group (hereinafter to be also referred to as thioether compound (103)) and an alcohol compound represented by the formula (105):

(105)

wherein $L^1$ is an alkylene group; and $D^1$ is an electron-withdrawing group, to a coupling reaction in the presence of a halogenating agent, a desiccant and a Lewis acid, and then distillation in the presence of at least one kind of additive selected from a sulfur-containing antioxidant and a maleimide group-containing compound.

Therefore, the present invention also provides a production method of thioether compound (104) by Step 0, and a production method of glycoside compound (Ib) by Step 0 and Step 1.

In the aforementioned chemical formula, B is more preferably bonded to the D-ribose skeleton in the aforementioned chemical formula (I) at the 9-position nitrogen when B is adenine, at the 1-position nitrogen when B is cytosine, at the 9-position nitrogen when B is guanine, at the 1-position nitrogen when B is uracil, or the 1-position nitrogen when B is thymine. The nucleic acid base for B is optionally substituted by any substituent, and may not be substituted. Examples of the substituent include halogen, acyl group (same as acyl group as the following amino-protecting group), alkyl group, aralkyl group, alkoxy group, alkoxyalkyl group, hydroxy group, amino group, monoalkylamino group (e.g., methylamino, ethylamino etc.), dialkylamino group (e.g., dimethylamino, diethylamino etc.), carboxy group, cyano group, nitro group and the like. The number of these substituents may be 0, 1 or more (e.g., 2-3) and, when multiple substituents are involved, one kind or plural kinds thereof may be used.

B may or may not have a protecting group. For example, when the aforementioned nucleic acid base for B has an amino group (amino substituent) outside the ring, the aforementioned amino group may be protected by a protecting group. The aforementioned amino-protecting group is not particularly limited and, for example, may be the same as the protecting group etc. used in known nucleic acids chemistry. Examples of the aforementioned amino-protecting group include acyl group. Examples of the aforementioned acyl group include benzoyl group, 4-methoxybenzoyl group, acetyl group, propionyl group, butyryl group, isobutyryl group, phenylacetyl group, phenoxyacetyl group, 4-tert-butylphenoxyacetyl group, 4-isopropylphenoxyacetyl group and the like. Other than acyl group, for example, a (dimethylamino)methylene group and the like can be mentioned.

B is preferably adenine, cytosine, guanine, uracil or thymine.

n is 0 or 1, preferably 1.

$R^{1a}$-$R^{1d}$ are the same or different and each is a hydrogen atom, an alkyl group or an alkoxy group. Preferably, they are all alkyl groups, more preferably alkyl groups having 1-6 carbon atoms, particularly preferably isopropyl groups.

m is a positive integer, preferably an integer of 1-10, more preferably 1 or 2, particularly preferably 1.

R and R' are the same or different and each is an alkyl group, an alkenyl group, an alkynyl group, an aryl group, an aralkyl group, a cycloalkyl group, a cycloalkenyl group, a cycloalkylalkyl group, a cycloalkenylalkyl group or an alkoxyalkyl group, preferably alkyl group, more preferably alkyl group having 1-6 carbon atoms, particularly preferably all methyl groups.

$L^1$ is an alkylene group, preferably an alkylene group having 1-6 carbon atoms, more preferably an ethylene group.

$D^1$ is an electron-withdrawing group, preferably cyano, nitro, alkylsulfonyl, halogen, arylsulfonyl, trihalomethyl or the like, more preferably a cyano group.

$R^{2a}$ and $R^{2b}$ are the same or different and each is a hydrogen atom or a substituent, preferably the same substituent, more preferably an alkyl group (preferably a straight chain or branched chain alkyl group having 1-4 carbon atoms, more preferably an isopropyl group).

$R^{2a}$ and $R^{2b}$ optionally form a ring together with a nitrogen atom bonded thereto, wherein the ring is a nitrogen-containing heterocycle, may or may not have nitrogen atom other than the aforementioned nitrogen atom, oxygen atom or sulfur atom, and may or may not further have a substituent. Specifically, 5- or 6-membered monocyclic aromatic heterocycle such as furan ring, thiophene ring, pyrrole ring, an oxazole ring, an isoxazole ring, thiazole ring, isothiazole ring, imidazole ring, pyrazole ring, 1,2,3-oxadiazole ring, 1,2,4-oxadiazole ring, 1,3,4-oxadiazole ring, furazan ring, 1,2,3-thiadiazole ring, 1,2,4-thiadiazole ring, 1,3,4-thiadiazole ring, 1,2,3-a triazole ring, 1,2,4-a triazole ring, tetrazole ring, a pyridine ring, a pyridazine ring, a pyrimidine ring, a pyrazine ring, triazine ring and the like, 3- to 8-membered saturated or unsaturated non-aromatic heterocycle such as oxirane ring, azetidine ring, oxetane ring, thietane ring, pyrrolidine ring, tetrahydrofuran ring, thioran ring, piperidine ring, tetrahydropyran ring, a morpholine ring, thiomorpholine ring, piperazine ring, 3-hexahydrocyclopenta[c]pyrrole ring, homopiperidine ring, homopiperazine ring and the like, and the like can be mentioned. It is preferably non-aromatic heterocycle, more preferably piperidine ring, a morpholine ring, pyrrolidine ring, thiomorpholine or the like.

$R^{2a}$ and $R^{2b}$ are preferably straight chain or branched chain alkyl group having 1-4 carbon atoms, more preferably isopropyl group.

$R^{2c}$ is a hydrogen atom, an electron-withdrawing group or a substituent optionally substituted by an electron-withdrawing group, preferably an electron-withdrawing group or a substituent optionally substituted by an electron-withdrawing group, more preferably a substituent optionally substituted by an electron-withdrawing group. Preferably, $R^{2c}$ is an alkyl group (preferably straight chain or branched chain alkyl group having 1-4 carbon atoms, more preferably ethyl group) optionally substituted by an electron-withdrawing group (preferably cyano group), particularly preferably a cyanoethyl group.

While the halogenating agent used in Step 0 is not particularly limited, chlorinating agent such as chlorine, hydrochloric acid, hydrogen chloride, thionyl chloride, sulfuryl chloride, mesyl chloride, phosphorus oxychloride, phosphorus trichloride, phosphorus pentachloride, N-chlorosuccinimide and the like; brominating agents such as N-bromosuccinimide, N-bromophthalimide, 1,3-dibromohydantoin, 5,5-dimethyl-1,3-dibromohydantoin and the like; iodinating agents such as iodine, sodium iodide, potassium iodide, N-iodo-succinimide, 1,3-diiodo-5,5-dimethyl-hydantoin and the like, and the like can be mentioned. It is preferably an iodinating agent, more preferably N-iodo-succinimide.

As the desiccant to be used in Step 0, one generally used in the pertinent field can be utilized without particular limitation, and it is preferably a molecular sieve.

As the Lewis acid to be used in Step 0, one generally used in the pertinent field can be utilized without particular limitation, and can be appropriately selected according to the starting material, reagent and the like to be used. Preferably, it is at least one selected from the group consisting of perfluoroalkylcarboxylic acid (e.g., trifluoroacetic acid), perfluoroalkylsulfonic acid (e.g., trifluoromethanesulfonic acid), alkylsulfonic acid (e.g., methanesulfonic acid, ethanesulfonic acid) and a salt thereof. More preferably, it is methanesulfonic acid, trifluoromethanesulfonic acid or a salt thereof (preferably silver salt), particularly preferably methansulfonic acid or a silver salt of trifluoromethanesulfonic acid.

The thioether compound (103) used in Step 0 is commercially available, or can be synthesized by reference to the method described in WO 2013/027843 and the like. The alcohol compound (105) used in Step 0 is commercially available, or can be synthesized by a method known per se.

In Step 0, the conditions of the coupling reaction of thioether compound (103) and alcohol compound (105)) are not particularly limited. While the reaction solvent for the aforementioned coupling reaction is not particularly limited, for example, ketones such as acetone, methyl ethyl ketone, acetophenone and the like, ethers such as diethyl ether, THF (tetrahydrofuran), dioxane and the like, nitriles such as acetonitrile etc., and the like can be mentioned. While the reaction time of the aforementioned coupling reaction is not particularly limited, it is, for example, 1-12 hr, preferably 1-8 hr, more preferably 1-4 hr. While the reaction temperature of the aforementioned coupling reaction is not particularly limited, the optimal conditions are preferably determined as appropriate according to the starting materials, reagents and the like to be used. It is, for example, −75 to 0° C., preferably −60 to −10° C., more preferably −50 to −40° C. The concentration of thioether compound (103) and alcohol compound (105) is not particularly limited, and can be appropriately determined. The substance amount ratio of thioether compound (103) and alcohol compound (105) is not particularly limited and may be, for example, a stoichiometric mixture ratio or any other ratio. The amount of other reaction substance to be used is not particularly limited. The number of moles of the alcohol compound (105) is, for example, 0.2- to 3-fold, preferably 0.2- to 1.5-fold, more preferably 0.5- to 1-fold, the number of moles of thioether compound (103). The number of moles of the halogenating agent (preferably iodinating agent) is, for example, 0.5- to 3-fold, preferably 0.5- to 1.5-fold, more preferably 0.5- to 1-fold, the number of moles of thioether compound (103). The number of moles of the aforementioned Lewis acid is, for example, 1- to 3-fold, preferably 1- to 2-fold, more preferably 1- to 1.5-fold, the number of moles of thioether compound (103). Depending on the kind of the Lewis acid to be used, the number of moles of the Lewis acid is, for example, 0.005- to 0.5-fold, preferably 0.01- to 0.1-fold, more preferably 0.025- to 0.035-fold, the number of moles of thioether compound (103). While the amount of the desiccant (preferably molecular sieves) to be used is not particularly limited, it is preferably used in excess against the aforementioned each reaction substance. The reaction conditions of the aforementioned coupling reaction may be appropriately determined by referring to the conditions of a coupling reaction of a known thioether compound and an alcohol compound and the like, or may be appropriately determined by referring to the conditions of the below-mentioned Examples.

Step 0 is characterized in that distillation is performed after the aforementioned coupling reaction. While the aforementioned distillation can be performed by a method known per se, it is preferably performed repeatedly under reduced pressure in the presence of at least one kind selected from a sulfur-containing antioxidant and a maleimide group-containing compound as additive, since a highly pure thioether compound (104) can be obtained. The sulfur-containing antioxidant is a compound having a sulfur atom in a molecule having an anti-oxidation action, and phenothiazine and the like can be mentioned. The maleimide group-containing compound is a compound having a maleimide group in a molecule, and maleimide, 4,4'-bismaleimidodiphenylmethane, bis(3-ethyl-5-methyl-4-maleimidephenyl)methane and the like can be mentioned. Preferred is 4,4'-bismaleimidodiphenylmethane. In the present invention, 4,4'-bismaleimidodiphenylmethane is preferably used as an additive in distillation. While the amount of the additive to be used is not particularly limited, it is used at 0.01- to 0.5-fold, preferably 0.05- to 0.4-fold, further preferably 0.1- to 0.3-fold weight, that of the reaction substance. Specifically, it can be performed by reference to the conditions of the below-mentioned Examples. The distillation can enhance the purity of thioether compound (104) to not less than 80%, preferably 90%, more preferably not less than 95%, further preferably not less than 98%.

While the halogenating agent to be used in Step 1 is not particularly limited, chlorinating agent such as chlorine, hydrochloric acid, hydrogen chloride, thionyl chloride, sulfuryl chloride, mesyl chloride, phosphorus oxychloride, phosphorus trichloride, phosphorus pentachloride, N-chlorosuccinimide and the like; brominating agents such as N-bromosuccinimide, N-bromophthalimide, 1,3-dibromohydantoin, 5,5-dimethyl-1,3-dibromohydantoin and the like; iodinating agents such as iodine, sodium iodide, potassium iodide, N-iodo-succinimide, 1,3-diiodo-5,5-dimethylhydantoin and the like, and the like can be mentioned. It is preferably an iodinating agent, more preferably 1,3-diiodo-5,5-dimethylhydantoin or iodine. In one preferable embodiment of the present invention, when the nucleic acid base of the atomic group having a nucleic acid base skeleton of B is cytosine, uracil or guanine, and the iodinating agent is 1,3-diiodo-5,5-dimethylhydantoin. In another preferable embodiment of the present invention, when the nucleic acid base of the atomic group having a nucleic acid base skeleton of B is adenine, the iodinating agent is iodine.

In Step 1, two or more kinds of halogenating agents may also be used. For example, when an iodinating agent (e.g., 1,3-diiodo-5,5-dimethylhydantoin) is used as a halogenating agent, iodine may or may not be used in combination.

As a desiccant to be used in Step 1, those generally used in the pertinent field can be utilized without particular limitation, and molecular sieve is preferably used.

As the Lewis acid to be used in Step 1, those generally used in the pertinent field can be utilized without particular limitation, and can be appropriately selected according to the starting materials, reagents and the like to be used. It is preferably at least one selected from the group consisting of perfluoroalkylcarboxylic acid (e.g., trifluoroacetic acid), perfluoroalkylsulfonic acid (e.g., trifluoromethanesulfonic acid), alkylsulfonic acid (e.g., methanesulfonic acid, ethanesulfonic acid) and a salt thereof. More preferably, it is methanesulfonic acid, trifluoromethanesulfonic acid or a salt thereof (preferably silver salt), particularly preferably methansulfonic acid or trifluoromethanesulfonic acid. In a preferable one embodiment of the present invention, when the nucleic acid base in the atomic group having a nucleic acid base skeleton for B is cytosine, uracil or guanine, the Lewis acid is trifluoromethanesulfonic acid. In another preferable one embodiment of the present invention, when the nucleic acid base in the atomic group having a nucleic acid base skeleton for B is adenine, the Lewis acid is methanesulfonic acid.

Glycoside compound (Ia) to be used in Step 1 is commercially available, or can be synthesized by a method known per se.

In Step 1, the conditions of the coupling reaction of glycoside compound (Ia) and thioether compound (104) are not particularly limited. While the reaction solvent for the aforementioned coupling reaction is not particularly limited, for example, ketones such as acetone, methyl ethyl ketone, acetophenone and the like, ethers such as diethyl ether, THF (tetrahydrofuran), dioxane and the like, nitriles such as acetonitrile etc., and the like can be mentioned. While the reaction time of the aforementioned coupling reaction is not particularly limited, it is, for example, 15 min-6 hr, preferably 15 min-2 hr, more preferably 30 min-1 hr. While the reaction temperature (flask inside temperature) of the aforementioned coupling reaction is not particularly limited, optimal conditions are determined as appropriate according to the starting materials, reagents and the like to be used. It is, for example, −90 to 0° C., preferably −70 to −20° C., more preferably −60 to −30° C. The concentration of glycoside compound (Ia) and thioether compound (104) is not particularly limited, and can be determined as appropriate. The substance amount ratio of glycoside compound (Ia) and thioether compound (104) is not particularly limited and may be, for example, a stoichiometric mixture ratio or any other ratio. Also, the amount of other reaction substance to be used is not particularly limited. The number of moles of thioether compound (104) is, for example, 1- to 5-fold, preferably 1- to 3-fold, 1- to 2-fold, the number of moles of glycoside compound (Ia). While the number of moles of the halogenating agent (preferably iodinating agent) varies depending on the kind of the halogenating agent to be used, it is generally, for example, 1- to 10-fold the number of moles of glycoside compound (Ia). When the halogenating agent is 1,3-diiodo-5,5-dimethylhydantoin, it is, for example, 1- to 5-fold, 1- to 3-fold, preferably 1- to 2-fold, more preferably 1- to 1.5-fold, the number of moles of glycoside compound (Ia). When the halogenating agent is iodine, it is, for example, 1- to 10-fold, preferably 2- to 10-fold, more preferably 4- to 8-fold, more preferably 5- to 6-fold, the number of moles of glycoside compound (Ia). The number of moles of the aforementioned Lewis acid is, for example, 1- to 3-fold, preferably 1- to 2-fold, more preferably 1- to 1.5-fold, the number of moles of glycoside compound (Ia). The reaction conditions of the aforementioned coupling reaction may be appropriately determined by referring to, for example, the conditions of a known amidite synthesis of the glycoside compound, and the like, or may be appropriately determined by referring to the conditions of the below-mentioned Examples.

In Step 1, the order of addition of halogenating agent, Lewis acid, thioether compound (104) and desiccant is not particularly limited. In one preferable embodiment of the present invention, when the nucleic acid base of the atomic group having a nucleic acid base skeleton of B is cytosine, uracil or guanine, thioether compound (104) is preferably added lastly in Step 1. That is, it is preferable to add a halogenating agent to a reaction system in the presence of a desiccant, successively add a Lewis acid, and add thioether compound (104). In another preferable one embodiment of the present invention, when the nucleic acid base of the atomic group having a nucleic acid base skeleton of B is adenine, the halogenating agent is preferably added lastly in Step 1. That is, it is preferable to add a Lewis acid to a reaction system in the presence of a desiccant, successively add thioether compound (104), and add a halogenating agent. The thioether compound (104), a halogenating agent, and a Lewis acid can be added to the reaction system at any intervals according to the above-mentioned order of addition, and the interval can be appropriately determined according to the amounts thereof to be charged and the like.

The production method of the present invention preferably further contains the following step (Step 2).

[Step 2]

A step of obtaining a glycoside compound represented by the formula (Ic):

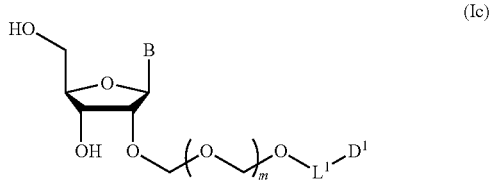

(Ic)

wherein each symbol is as defined in Step 1 (hereinafter to be also referred to as glycoside compound (Ic)) by deprotecting glycoside compound (Ib).

Therefore, the present invention also provides a method of producing glycoside compound (Ic) by the above-mentioned Step 2 (more specifically the above-mentioned Step 0, Step 1 and subsequent Step 2).

In Step 2, while the conditions of the deprotection are not particularly limited, for example, a known deprotecting agent can be used. While the aforementioned deprotecting agent is not particularly limited, for example, hydrogen fluoride pyridine, triethylamine trihydrofluoride, ammonium fluoride, hydrofluoric acid, tetrabutylammonium fluoride and the like can be mentioned. While the reaction solvent for the deprotection is not particularly limited, for example, ketones such as acetone and the like, ethers such as diethyl ether, THF (tetrahydrofuran) and the like, alcohols such as methanol, ethanol and the like, nitriles such as acetonitrile etc., and the like can be mentioned. While the reaction time of the deprotection is not particularly limited, it is, for example, 30 min-24 hr, preferably 2-12 hr, more preferably 2-4 hr. While the reaction temperature of the deprotection is not particularly limited, it is, for example, 0 to 100° C., preferably 20 to 60° C., more preferably 20 to 50° C. The concentration of the glycoside compound (Ib) and the deprotecting agent is not particularly limited, and can be appropriately determined. The substance amount ratio of the glycoside compound (Ib) and the deprotecting agent is not particularly limited and may be, for example, a stoichiometric mixture ratio or any other ratio. Also, the amount of other reaction substance to be used is not particularly limited. The number of moles of the deprotecting agent is, for example, 0.1- to 20-fold, preferably 0.2- to 10-fold, more preferably 1- to 5-fold, the number of moles of the glycoside compound (Ib). The reaction conditions of the deprotection may be appropriately determined by referring to, for example, the conditions of a similar deprotection in a known glycoside compound, and the like, or by reference to the below-mentioned Examples.

The production method of the present invention preferably further contains the following step (Step 3).

[Step 3]

A step of obtaining a glycoside compound represented by the formula (Id):

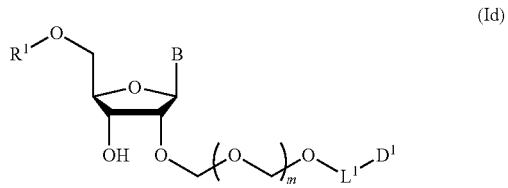

(Id)

wherein $R^1$ is a hydroxyl-protecting group, and other symbols are as defined in Step 1 (hereinafter to be also referred to as glycoside compound (Id)) by introducing a hydroxyl-protecting group into glycoside compound (Ic).

Therefore, the present invention also provides a method of producing glycoside compound (Id) by the above-mentioned Step 3 (more specifically the above-mentioned Step 0, Step 1, Step 2 and subsequent Step 3).

In the formula (Id), while the hydroxyl-protecting group is not particularly limited, it is preferably an alkyl-type protecting group such as a methyl group, a tert-butyl group, a benzyl group, a trityl group and the like; an ether-type protecting group such as a tetrahydropyranyl group, a methoxymethyl group and the like; a carbonate-type protecting group such as a methylcarbonate group, an ethylcarbonate group and the like; a silicon-based protecting group such as a trimethylsilyl group, a tert-butyldimethylsilyl group, a tert-butyldiphenylsilyl group and the like, and the like, with preference given to 4,4'-dimethoxytrityl (DMTr).

The reaction conditions of the aforementioned protecting group introduction step are not particularly limited and may be appropriately determined, for example, by referring to a similar reaction in a known glycoside compound and the like.

In an introduction reaction of the protecting group $R^1$, a protecting group-introducing agent may be appropriately selected according to $R^1$. For example, when the protecting group is 4,4'-dimethoxytrityl, 4,4'-dimethoxytrityl chloride can be used as a protecting group introduction agent.

While the reaction solvent is not particularly limited, for example, polar solvents such as pyridine and the like, nitriles such as acetonitrile and the like, ethers such as tetrahydrofuran etc., and the like can be mentioned. While the reaction time is not particularly limited, it is, for example, 30 min-24 hr, preferably 2-12 hr, more preferably 2-4 hr. While the reaction temperature is not particularly limited, it is, for example, 0 to 100° C., preferably 10 to 60° C., more preferably 20 to 30° C. The concentration of the glycoside compound (Ic) and the protecting group-introducing agent to be used is not particularly limited, and can be appropriately determined. The substance amount ratio of the glycoside compound (Ic) and the protecting group-introducing agent is not particularly limited and may be, for example, a stoichiometric mixture ratio or any other ratio. Also, the amount of other reaction substance to be used is not particularly limited. The number of moles of the protecting group-introducing agent is, for example, 1- to 100-fold, preferably 1- to 20-fold, more preferably 1- to 5-fold, the number of moles of the glycoside compound (Ic). The reaction conditions of the introduction reaction of a protecting group $R^1$ may be appropriately determined by referring to, for example, the conditions of a similar reaction in a known glycoside compound, and the like, or by reference to the below-mentioned Examples.

The production method of the present invention preferably further contains the following step (Step 4).

[Step 4]

A step of obtaining glycoside compound (I) by phosphorylating glycoside compound (Id).

Therefore, the present invention also provides a method of producing glycoside compound (I) by the above-mentioned Step (more specifically the above-mentioned Step 0, Step 1, Step 2, Step 3 and subsequent Step 4).

The phosphorylation of glycoside compound (Id) in Step 4 is performed by reaction with the following compound.

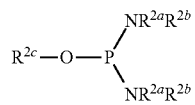

wherein $R^{2a}$ and $R^{2b}$ are the same or different and each is a hydrogen atom or a substituent; $R^{2c}$ is a hydrogen atom, an electron-withdrawing group or a substituent optionally substituted by an electron-withdrawing group; and $R^{2a}$ and $R^{2b}$ optionally form a ring together with a nitrogen atom bonded thereto.

The two $R^{2a}$ may be the same or different and are preferably the same. The two $R^{2b}$ may be the same or different and are preferably the same. $R^{2a}$ and $R^{2b}$ may be the same or different and are preferably the same, more preferably substituents, particularly preferably alkyl groups, particularly preferably isopropyl groups.

$R^{2c}$ is preferably an electron-withdrawing group or a substituent optionally substituted by electron-withdrawing group, more preferably a substituent optionally substituted by an electron-withdrawing group, particularly preferably a straight chain or branched chain alkyl group having 1-4 carbon atoms (e.g., ethyl) optionally substituted by an electron-withdrawing group. As the electron-withdrawing group, cyano is preferable.

$R^{2c}$ is preferably a cyanoethyl group.

When an isomer such as enantiomer, tautomer or stereoisomer (e.g., geometric isomer, conformational isomer and optical isomer) and the like is present in the compounds such as glycoside compound, thioether and the like to be used in the present invention, or provided by the present invention (hereinafter sometimes to be simply referred to as "the compound of the present invention"), all isomers are encompassed in the compound of the present invention. For example, while the chemical formulas showing the glycoside compounds of the present invention depicts as if the sugar skeleton of glycoside is D-ribose, it may be an enantiomer thereof, i.e., L-ribose. When the compound of the present invention can form a salt, such salt is also encompassed in the compound of the present invention. The aforementioned salt of the compound of the present invention may be an acid addition salt or a base addition salt. Furthermore, an acid that forms the aforementioned acid addition salt may be an inorganic acid or an organic acid, and a base that forms the aforementioned base addition salt may be an inorganic base or an organic base. While the aforementioned inorganic acid is not particularly limited, for example, sulfuric acid, phosphoric acid, hydrofluoric acid, hydrochloric acid, hydrobromic acid, hydroiodic acid, hypofluorous acid, hypochlorous acid, hypobromous acid, hypoiodous acid, fluorous acid, chlorous acid, bromous acid, iodous acid, fluorine acid, chlorine acid, bromine acid, iodine acid, perfluoric acid, perchloric acid, perbromic acid, periodic acid and the like can be mentioned. While the aforementioned organic acid is not particularly limited, for example, p-toluenesulfonic acid, methanesulfonic acid, oxalic acid, p-bromobenzenesulfonic acid, carbonic acid, succinic acid, citric acid, benzoic acid, acetic acid and the like can be mentioned. While the aforementioned inorganic base is not particularly limited, for example, ammonium hydroxide, alkali metal hydroxide, alkaline earth metal hydroxide, carbonate and hydrogencarbonates and the like can be mentioned and, more specifically, for example, sodium hydroxide, potassium hydroxide, potassium carbonate, sodium carbonate, sodium hydrogen carbonate, potassium hydrogen carbonate, calcium hydroxide and calcium carbonate and the like can be mentioned. The aforementioned organic base is not particularly limited and, for example, ethanolamine, triethylamine and tris(hydroxymethyl)aminomethane and the like can be mentioned. The production method of these salts is not particularly limited.

While the present invention is explained in more detail in the following by referring to Examples, they do not limit the scope of the present invention.

List of Abbreviations:
EMM: cyanoethoxymethoxymethyl
DIH: 1,3-diiodo-5,5-dimethylhydantoin
TfOH: trifluoromethanesulfonic acid
MS4A: molecular sieves 4A
THF: tetrahydrofuran
TEA.3HF: triethylamine trihydrofluoride
DMTr: 4,4'-dimethoxytrityl
iPr: isopropyl
NIS: N-iodosuccinimide
AgOTf: silver trifluoromethanesulfonate
EtOH: ethanol

EXAMPLES

Production Example 1

Synthesis of EMM Reagent (1004)

According to the following scheme, an EMM reagent (1004) was synthesized. "EMM" stands for "cyanoethoxymethoxymethyl" (hereinafter the same).

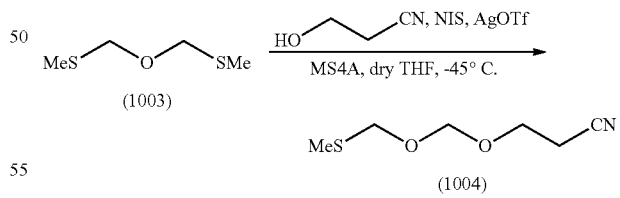

Synthesis of 2-cyanoethoxymethylmethylthiomethylether (1004)

Commercially available bis(methylthiomethyl)ether (1003) (30 g, 217 mmol) was dissolved in tetrahydrofuran (300 mL) under an argon atmosphere. To the solution thereof were added cyanoethanol (15 g, 217 mmol, purified by evaporation under reduced pressure) and molecular sieves 4A (30 g), and the mixture was stirred for 10 min. N-iodosuccinimide (49 g, 217 mmol) was dissolved in the mixture, and the mixture was immediately cooled to −45° C. After cooling, silver trifluoromethanesulfonate (1.7 g, 6.5 mmol) was added and the mixture was stirred for 3 hr. After stirring, ice-cooled 10% aqueous sodium thiosulfate solution was added, and the mixture was vigorously stirred at −45° C. After 10 min, the mixture was taken out from the cooling bath, ethyl acetate was added and the mixture was vigorously stirred for 30 min. The reaction solution was filtered through celite. The filtrate was washed with 10% aqueous sodium thiosulfate solution, saturated aqueous sodium hydrogen carbonate solution and saturated aqueous sodium chloride solution in this order. Thereafter, the organic layer was separated, dried over anhydrous sodium sulfate, and concentrated under reduced pressure. The above-mentioned reaction was performed 5 times to give a crude product (150 g). To the crude product was added 4,4'-bismaleimidodiphenylmethane (33 g) and the mixture was evaporated under reduced pressure at 0.50 mmHg to give a crude purification product (71 g, boiling point 93-96° C.) as a main distillate. To the obtained crude purification product (71 g) was added 4,4'-bismaleimidodiphenylmethane (15 g) and the mixture was evaporated under reduced pressure at 0.25 mmHg to give the object compound (50 g, boiling point 83-86° C., purity 98.46%) as a main distillate.

Compound (1004):

$^1$H-NMR (400 MHz, CDCl$_3$) δ: 4.86 (2H, s), 4.73 (2H, s), 3.80 (2H, t, J=6.3 Hz), 2.64 (2H, t, J=6.3 Hz), 2.18 (3H, s).

Example 1

Synthesis of Cytidine EMM Amidite (I-1)

According to the following scheme, cytidine EMM amidite (I-1) was synthesized.

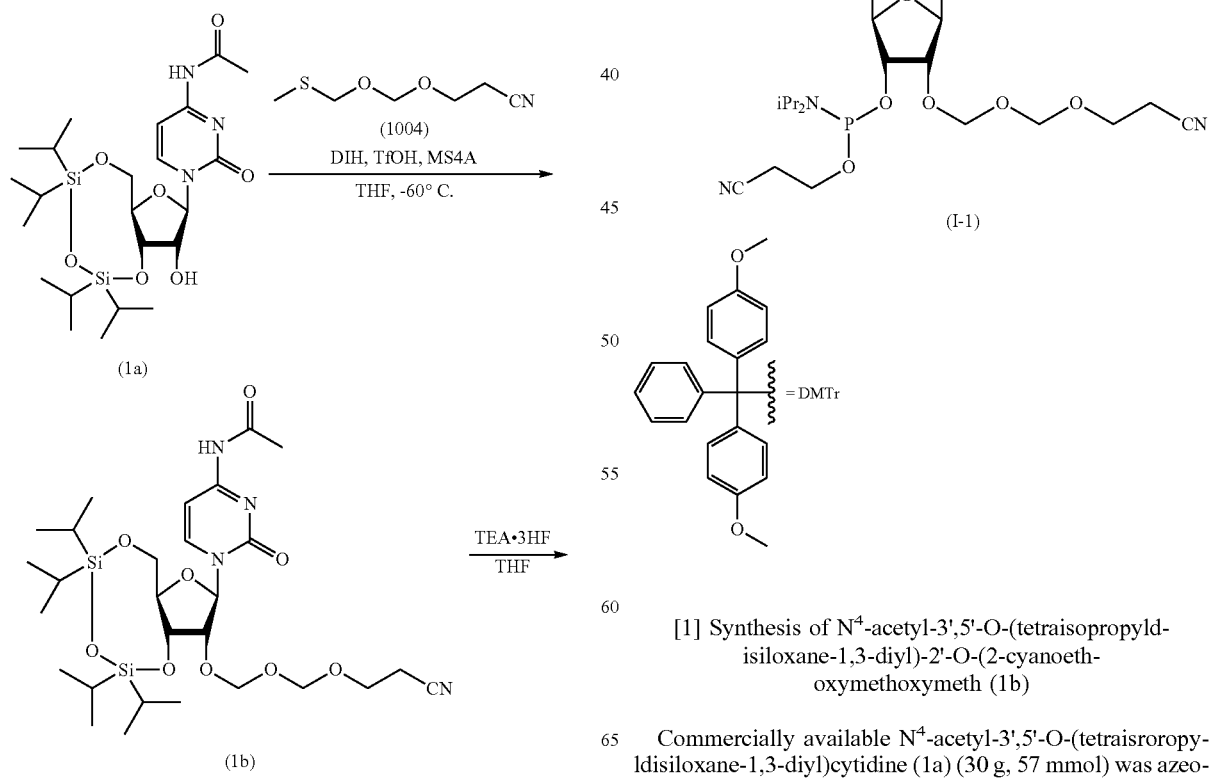

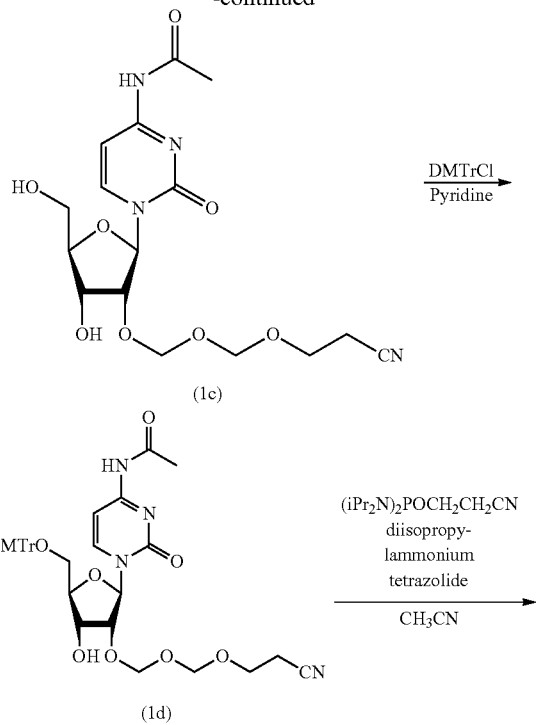

[1] Synthesis of N$^4$-acetyl-3',5'-O-(tetraisopropyldisiloxane-1,3-diyl)-2'-O-(2-cyanoethoxymethoxymeth (1b)

Commercially available N$^4$-acetyl-3',5'-O-(tetraisropyldisiloxane-1,3-diyl)cytidine (1a) (30 g, 57 mmol) was azeotropically distilled twice with toluene and once with tetrahydrofuran, and dried in vacuo. Under an argon atmosphere, the dried product was dissolved in tetrahydrofuran (180 mL), molecular sieves 4A (30 g) and 1,3-diiodo-5,5-dimethylhydantoin (33 g, 85 mmol) were added, the mixture was stirred for 5 min. 2-Cyanoethoxymethylmethythioethylether (1004) (14 g, 85 mmol) was added at a flask inside temperature of −60° C. and the mixture was stirred at −60° C. for 30 min. After completion of the reaction, to the reaction solution was added a cooled mixed solution of aqueous saturated sodium thiosulfate solution and saturated aqueous sodium hydrogen carbonate solution. The mixture was vigorously stirred until the brown color disappeared. The mixture was extracted with ethyl acetate, and the organic layer was washed twice with saturated aqueous sodium thiosulfate solution, once with saturated aqueous sodium hydrogen carbonate solution, and once with saturated aqueous sodium chloride solution. The organic layer after washing was dried over anhydrous sodium sulfate, and concentrated under reduced pressure to give the object compound (1b) as a crude product (45 g, purity 93.8%). The instrumental analytical values of the compound (1b) are shown below.

Compound (1b):

$^1$H-NMR (400 MHz, CDCl$_3$) δ: 9.17 (1H, s), 8.30 (1H, d, J=7.2 Hz), 7.41 (1H, d, J=7.8 Hz), 5.79 (1H, s), 5.18 (1H, d, J=6.8 Hz), 5.03 (d, 1H, J=7.4 Hz), 4.29 (1H, d, J=13.7 Hz), 4.23-4.10 (5H, m), 4.03-3.96 (2H, m), 3.87-3.75 (1H, m), 2.76-2.65 (2H, m), 2.24 (3H, s), 1.11-0.89 (28H, m).

[2] Synthesis of N$^4$-acetyl-2'-O-(2-cyanoethoxymethoxymethyl)cytidine (1c)

N$^4$-acetyl-3',5'-O-(tetraisopropyldisiloxane-1,3-diyl)-2'-O-(2-cyanoethoxymethoxymethyl)cytidine (1b) (45 g) was dissolved in tetrahydrofuran (240 mL) under an argon atmosphere. To the solution was added triethylamine trihydrofluoride (13 mL, 81 mmol), and the mixture was stirred at room temperature for 2 hr. The reaction solution was cooled to 0° C., and the resulting precipitate was collected by filtration. Vacuum drying gave the object compound (1c) as a white precipitate (15 g, purity 97.7%, two-step yield 66%). The instrumental analytical values of compound (1c) are shown below.

Compound (1c):

$^1$H-NMR (400 MHz, D$_2$O) δ: 8.24 (1H, d, J=7.3 Hz), 7.24 (1H, d, J=7.8 Hz), 5.92 (1H, d, J=2.4 Hz), 5.02 (1H, d, J=6.8 Hz), 4.89 (1H, d, J=6.8 Hz), 4.79-4.74 (2H, m), 4.29 (1H, dd, J=4.9, 2.9 Hz), 4.17 (1H, t, J=6.3 Hz), 4.09-4.05 (1H, m), 3.90-3.85 (1H, m), 3.77-3.70 (3H, m), 2.67 (2H, t, J=6.1 Hz), 2.12 (3H, s).

melting point: 171-172° C.

[3] Synthesis of N$^4$-acetyl-5'-O-(4,4'-dimethoxytrityl)-2'-O-(2-cyanoethoxymethoxymethyl)cytidine (1d)

N$^4$-acetyl-2'-O-(2-cyanoethoxymethoxymethyl) cytidine (1c) (15 g, 38 mmol) was azeotropically distilled with pyridine, and dried in vacuo. The residue was dissolved in pyridine (200 mL), 4,4'-dimethoxytrityl chloride (19 g, 57 mmol) was added at 0° C. and the mixture was stirred at room temperature for 4 hr. After completion of the reaction, methanol was added and the mixture was stirred for 30 min, and the solvent was evaporated under reduced pressure. To the residue was added dichloromethane and the mixture was washed twice with saturated aqueous sodium hydrogen carbonate solution and once with saturated aqueous sodium chloride solution. The organic layer after washing was dried over anhydrous sodium sulfate and concentrated under reduced pressure. The obtained crude product was purified by silica gel column chromatography (ethyl acetate, containing 0.05% pyridine→ethyl acetate:acetone=1:1, containing 0.05% pyridine) to give the object compound (1d) (23 g, purity 99.2%, yield 86%). The instrumental analytical values of compound (1d) are shown below.

Compound (1d):

$^1$H-NMR (400 MHz, CDCl$_3$) δ: 8.61 (1H, br. s), 8.49 (1H, d, J=7.8 Hz), 7.42-7.26 (9H, m), 7.09 (1H, d, J=7.3 Hz), 6.88-6.86 (4H, m), 5.94 (1H, s), 5.35 (1H, d, J=6.8 Hz), 5.11 (1H, d, J=6.8 Hz), 4.92 (1H, d, J=7.3 Hz), 4.87 (1H, d, J=7.3 Hz), 4.49-4.40 (1H, m), 4.29 (1H, d, J=4.9 Hz), 4.15-4.08 (1H, m), 3.86 (t, 2H, J=6.2 Hz), 3.82 (s, 6H), 3.63 (dd, 1H, J=10.6, 2.6 Hz), 3.55 (dd, 1H, J=10.6, 2.6 Hz), 2.64 (2H, t, J=6.3 Hz), 2.56 (d, 1H, J=8.8 Hz), 2.21 (3H, s).

[4] Synthesis of N$^4$-acetyl-5'-O-(4,4'-dimethoxytrityl)-2'-O-(2-cyanoethoxymethoxymethyl)cytidine 3'-O-(2-cyanoethyl N,N-diisopropylphosphoramidite) (I-1)

N$^4$-acetyl-5'-O-(4,4'-dimethoxytrityl)-2'-O-(2-cyanoethoxymethoxymethyl)cytidine (1d) (23 g, 31 mmol) was azeotropically distilled with acetonitrile, and dried in vacuo. This operation was performed twice. Under an argon atmosphere, diisopropylammoniumtetrazolide (6.5 g, 38 mmol) and acetonitrile (80 mL) were added, 2-cyanoethyl-N,N,N',N'-tetraisopropylphosphordiamidite (12 mL, 38 mmol) was further added, and the mixture was stirred at 40° C. for 3 hr. After completion of the reaction, the solvent was evaporated under reduced pressure. Ethyl acetate was added and the mixture was washed once with saturated aqueous sodium hydrogen carbonate solution and once with saturated aqueous sodium chloride solution. The organic layer after washing was dried over anhydrous sodium sulfate and concentrated under reduced pressure. The obtained crude product was purified by silica gel column chromatography (hexane:acetone=2:1, containing 0.1% triethylamine) to give the object compound (I-1) (25 g, purity 98.8%, yield 88%). The instrumental analytical values of compound (I-1) are shown below.

Compound (I-1):

$^{31}$P-NMR (162 MHz, CDCl$_3$) δ: 151.8, 150.3. MS(ESI+): m/z 923[M+Na]$^+$

Example 2

Synthesis of Uridine EMM Amidite (I-2)

Uridine EMM amidite (I-2) was synthesized according to the following scheme.

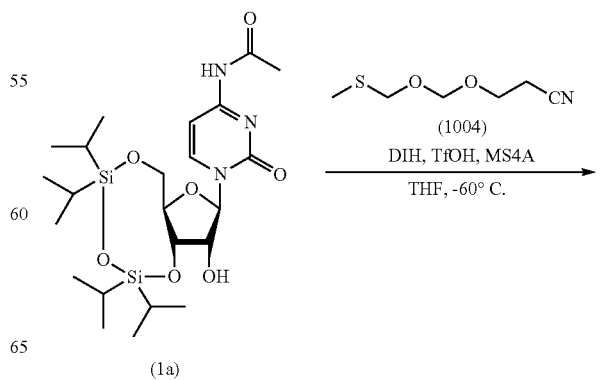

29
-continued

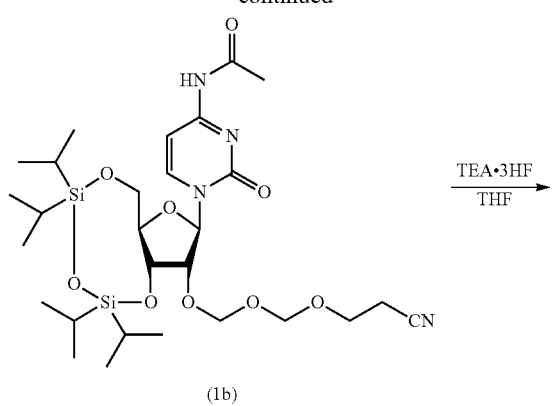
(1b)

TEA·3HF
THF
→

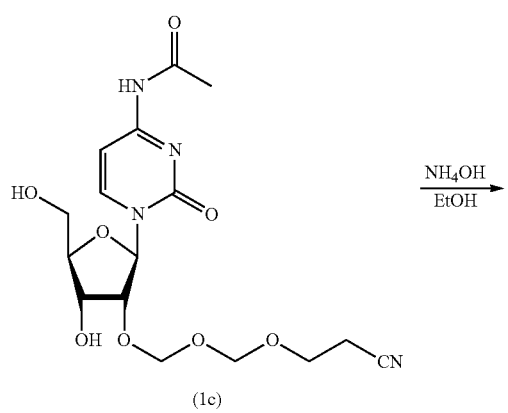
(1c)

NH₄OH
EtOH
→

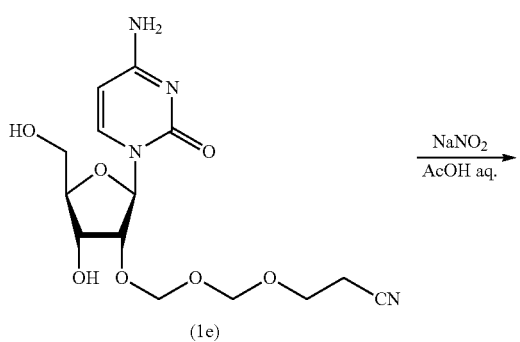
(1e)

NaNO₂
AcOH aq.
→

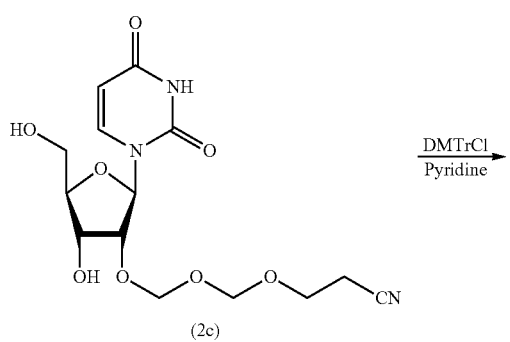
(2c)

DMTrCl
Pyridine
→

30
-continued

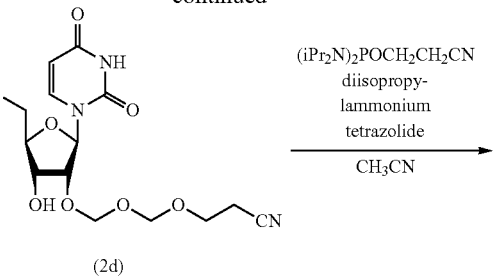
(2d)

(iPr₂N)₂POCH₂CH₂CN
diisopropy-
lammonium
tetrazolide
CH₃CN
→

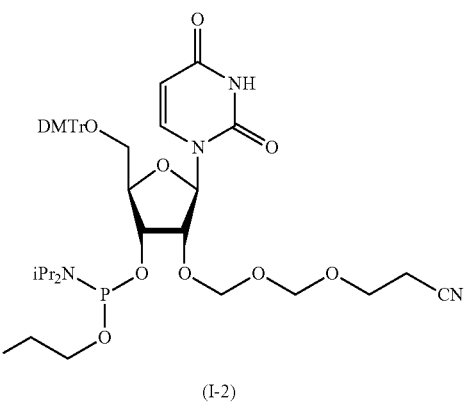
(I-2)

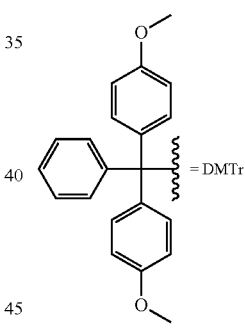
= DMTr

[1] Synthesis of N⁴-acetyl-3',5'-O-(tetraisopropyld-isiloxane-1,3-diyl)-2'-O-(2-cyanoethoxymethoxym-ethyl) cytidine (1b)

Commercially available N⁴-acetyl-3',5'-O-(tetraisopropyldisiloxane-1,3-diyl)cytidine (1a) (1.0 g, 1.9 mmol) was azeotropically distilled twice with toluene and once with tetrahydrofuran, and dried in vacuo. Under an argon atmosphere, the dried product was dissolved in tetrahydrofuran (6.0 mL), molecular sieves 4A (1.0 g) and 1,3-diiodo-5,5-dimethylhydantoin (1.1 g, 2.9 mmol) were added, the mixture was stirred, cooled to −60° C. Trifluoromethanesulfonic acid (0.25 mL, 2.9 mmol) was added dropwise at −60° C. and the mixture was stirred for 5 min. 2-Cyanoethoxymeth-ylmethylthiomethylether (1004) (0.46 g, 2.9 mmol) was added at a flask inside temperature of −60° C. and the mixture was stirred at −60° C. for 30 min. After completion of the reaction, to the reaction solution was added the cooled mixed solution of aqueous saturated sodium thiosulfate solution and saturated aqueous sodium hydrogen carbonate solution. The mixture was vigorously stirred until the brown color disappeared. The mixture was extracted with ethyl acetate, and the organic layer was washed twice with saturated aqueous sodium thiosulfate solution, once with saturated aqueous sodium hydrogen carbonate solution, and once with saturated aqueous sodium chloride solution. The organic layer after washing was dried over anhydrous sodium sulfate, and concentrated under reduced pressure to give the object compound (1b) as a crude product (1.2 g, purity 95.9%).

[2] Synthesis of $N^4$-acetyl-2'-O-(2-cyanoethoxymethoxymethyl)cytidine (1c)

$N^4$-acetyl-3',5'-O-(tetraisopropyldisiloxane-1,3-diyl)-2'-O-(2-cyanoethoxymethoxymethyl)cytidine (Ib) (1.2 g) was dissolved in tetrahydrofuran (8.0 mL) under an argon atmosphere. To the solution was added triethylamine trihydrofluoride (0.40 mL, 2.5 mmol), and the mixture was stirred at room temperature for 2 hr. The reaction solution was cooled to 0° C., and the resulting precipitate was collected by filtration. Vacuum drying gave the object compound (1c) as a white precipitate (0.46 g, purity 98.7%, two-step yield 61%).

[3] Synthesis of 2'-O-(2-cyanoethoxymethoxymethyl)cytidine (1e)

$N^4$-acetyl-2'-O-(2-cyanoethoxymethoxymethyl) cytidine (1c) (0.46 g, 1.2 mmol) was dissolved in ethanol (8.4 mL). To the solution were added water (6.3 mL) and conc. aqueous ammonia (2.1 mL) and the mixture was stood overnight at 4° C. After completion of the reaction, the solvent was evaporated under reduced pressure to give the object compound (1e) as a crude product (0.53 g).

[4] Synthesis of 2'-O-(2-cyanoethoxymethoxymethyl)uridine(2c)

2'-O-(2-cyanoethoxymethoxymethyl) cytidine (1e) (0.53 g, 1.5 mmol) was dissolved in water (10 mL). To the solution were added sodium nitrite (1.6 g, 22.5 mmol) and acetic acid (2.5 mL) and the mixture was stirred at 40° C. for 4 hr, and at room temperature overnight. After completion of the reaction, the solvent was evaporated under reduced pressure. To the residue was added pyridine and the mixture was filtered under reduced pressure. The mother liquor was evaporated under reduced pressure to give the object compound (2c) as a crude product (0.8 g). The instrumental analytical values of compound (2c) are shown below.
Compound (2c):
$^1$H-NMR (400 MHz, CDCl$_3$) d: 10.23 (1H, br. s), 7.90 (1H, d, J=7.8 Hz), 5.84 (1H, d, J=2.9 Hz), 5.59 (1H, d, J=8.3 Hz), 5.09 (1H, d, J=7.0 Hz), 4.98 (1H, d, J=6.7 Hz), 4.87 (2H, s), 4.25-4.22 (3H, m), 3.99 (1H, s), 3.83-3.69 (5H, m), 2.70-2.61 (2H, m).
melting point: 162-163° C.

[5] Synthesis of 5'-O-(4,4'-dimethoxytrityl)-2'-O-(2-cyanoethoxymethoxymethyl) uridine (2d)

2'-O-(2-cyanoethoxymethoxymethyl)uridine(2c) (0.8 g, 2.2 mmol) was azeotropically distilled with pyridine, and dried in vacuo. The residue was dissolved in pyridine (13 mL), 4,4'-dimethoxytrityl chloride (895 mg, 2.6 mmol) was added and the mixture was stirred at room temperature for 2 hr. After completion of the reaction, the solvent was evaporated to half under reduced pressure. To the residue was added dichloromethane and the mixture was washed twice with saturated aqueous sodium hydrogen carbonate solution and once with saturated aqueous sodium chloride solution. The organic layer after washing was dried over anhydrous sodium sulfate and concentrated under reduced pressure. The obtained crude product was purified by silica gel column chromatography (ethyl acetate:hexane=2:1, containing 0.05% pyridine) to give the object compound (690 mg, purity 99.89%, 3 step yield 90%). The instrumental analytical values of compound (2d) are shown below.

Compound (2d):
$^1$H-NMR (400 MHz, CDCl$_3$) δ: 8.62 (1H, br. s), 7.99 (1H, d, J=7.8 Hz), 7.40-7.25 (9H, m), 6.90-6.84 (4H, m), 5.96 (1H, d, J=2.0 Hz), 5.28 (1H, d, J=8.3 Hz), 5.18 (1H, d, J=6.8 Hz), 5.03 (1H, d, J=7.3 Hz), 4.87 (2H, d, J=7.3 Hz), 4.48 (1H, q, J=5.4 Hz), 4.29 (1H, dd, J=5.1, 2.2 Hz), 4.11-4.07 (1H, m), 3.87 (2H, t, J=6.0 Hz), 3.84 (6H, s), 3.55 (2H, dd, J=9.0, 2.2 Hz), 2.76 (1H, d, J=7.8 Hz), 2.65 (2H, t, J=6.6 Hz).

[6] Synthesis of 5'-O-(4,4'-dimethoxytrityl)-2'-O-(2-cyanoethoxymethoxymethyl)uridine 3'-O-(2-cyanoethyl N,N-diisopropylphosphoramidite) (I-2)

5'-(4,4'-dimethoxytrityl)-2'-O-(2-cyanoethoxymethoxymethyl)uridine (2d) (690 mg, 1.0 mmol)) was azeotropically distilled with acetonitrile, and dried in vacuo. This operation was performed twice. Under an argon atmosphere, diisopropylammoniumtetrazolide (205 mg, 1.2 mmol) and acetonitrile (5 mL) were added, 2-cyanoethyl-N,N,N',N'-tetraisopropylphosphordiamidite (362 mg, 1.2 mmol) was further added, and the mixture was stirred at 40° C. for 2 hr. After completion of the reaction, the solvent was evaporated under reduced pressure. Dichloromethane was added and the mixture was washed once with saturated aqueous sodium hydrogen carbonate solution and once with saturated aqueous sodium chloride solution. The organic layer after washing was dried over anhydrous sodium sulfate and concentrated under reduced pressure. The obtained crude product was purified by silica gel column chromatography (hexane:acetone=1:1, containing 0.1% triethylamine) to give the object compound (I-2) (804 mg, purity 98.4%, yield 89%). The instrumental analytical values of compound (I-2) are shown below.

Compound (I-2):
$^{31}$P-NMR (162 MHz, CDCl$_3$) δ: 153.5, 151.9.

Example 3

Synthesis of Guanosine EMM Amidite (I-3)

Guanosine EMM amidite (I-3) was synthesized according to the following scheme.

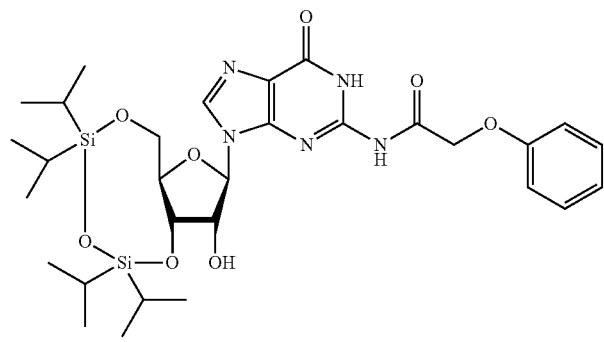
(3a)
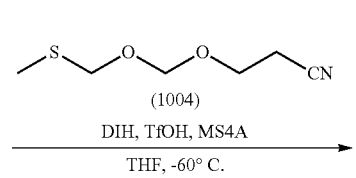
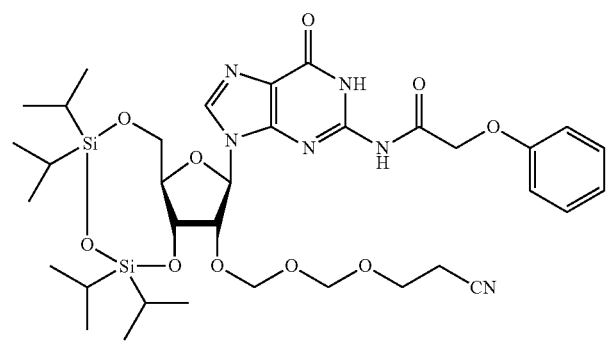
(3b)
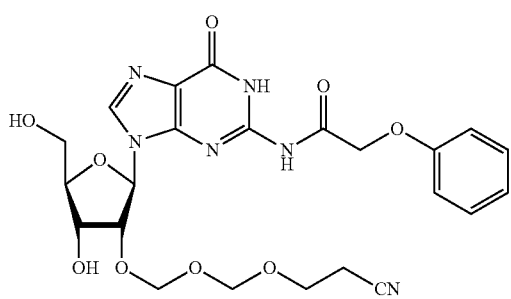
(3c)
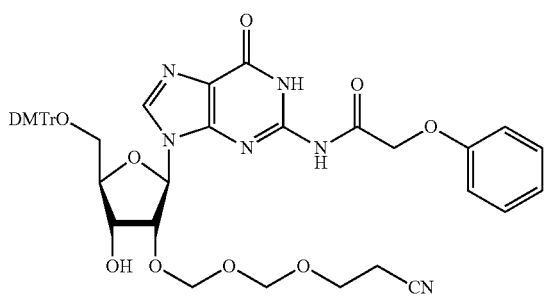
(3d)

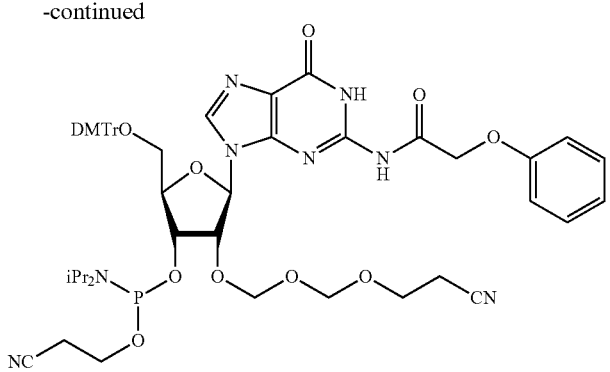

(I-3)

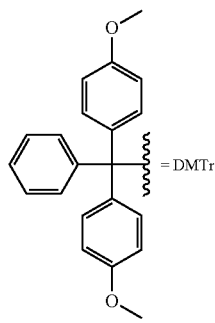 = DMTr

[1] Synthesis of N²-phenoxyacetyl-3',5'-O-(tetraisopropyldisiloxane-1,3-diyl)-2'-O-(2-cyanoethoxymethoxymethyl)guanosine (3b)

Commercially available N²-phenoxyacetyl-3',5'-O-(tetraisopropyldisiloxane-1,3-diyl)guanosine (3a) (1.0 g, 1.5 mmol) was dissolved in tetrahydrofuran and the mixture was azeotropically distilled twice with toluene and once with tetrahydrofuran, and dried in vacuo. Under an argon atmosphere, the dried product was dissolved in tetrahydrofuran (6.0 mL), molecular sieves 4A (1.0 g) was added, 1,3-diiodo-5,5-dimethylhydantoin (0.87 g, 2.3 mmol) was added and the mixture was stirred at room temperature. The mixture was cooled to −60° C. and stirred for 5 min. Trifluoromethanesulfonic acid (0.2 mL, 2.3 mmol) was added dropwise. The mixture was stirred for 5 min, 2-cyanoethoxymethylmethylthiomethylether (1004) (0.37 g, 2.3 mmol) was added at a flask inside temperature of −60° C. and the mixture was stirred at −60° C. for 30 min. After completion of the reaction, to the reaction solution was added a cooled mixed solution of aqueous saturated sodium thiosulfate solution and saturated aqueous sodium hydrogen carbonate solution. The mixture was vigorously stirred until the brown color disappeared. The mixture was extracted with ethyl acetate, and the organic layer was washed twice with saturated aqueous sodium thiosulfate solution, once with saturated aqueous sodium hydrogen carbonate solution, and once with saturated aqueous sodium chloride solution. The organic layer after washing was dried over anhydrous sodium sulfate, and concentrated under reduced pressure to give the object compound (3b) as a crude product (1.3 g, purity 88.9%). The instrumental analytical values of compound (3b) are shown below.

Compound (3b):

¹H-NMR (400 MHz, CDCl₃) δ: 11.79 (1H, s), 9.11 (1H, s), 8.04 (1H, s), 7.41-7.34 (2H, m), 7.13-6.97 (3H, m), 5.94 (1H, s), 5.08, 4.97 (2H, 2d, J=7.2 Hz), 4.87-4.67 (2H, m), 4.51-4.46 (1H, dd, J=9.3, 4.9 Hz), 4.33-4.24 (2H, m), 4.15 (1H, d, J=9.3 Hz), 4.02 (1H, dd, J=13.2, 2.4 Hz), 3.77-3.71 (2H, m), 2.76-2.53 (2H, m), 1.11-0.94 (28H, m).

[2] Synthesis of N²-phenoxyacetyl-2'-O-(2-cyanoethoxymethoxymethyl)guanosine (3c)

N²-phenoxyacetyl-3',5'-O-(tetraisopropyldisiloxane-1,3-diyl)-2'-O-(2-cyanoethoxymethoxymethyl)guanosine (3b) (1.3 g, 1.7 mmol) was dissolved in tetrahydrofuran (5 mL) under an argon atmosphere. To the solution were added triethylamine trihydrofluoride (0.33 mL, 2.0 mmol) and the mixture was stirred at 35° C. for 2 hr. The reaction mixture was immersed in an ice bath at 0° C., water (4 mL) was added and the mixture was stirred for 10 min. Isopropyl ether (30 mL) was added and the mixture was stirred for 30 min. White precipitate was collected by filtration under reduced pressure and dried in vacuo to give the object compound (3c) (0.63 g, purity 89.76%). The instrumental analytical values of compound (3c) are shown below.

Compound (3c):

¹H-NMR (400 MHz, DMSO-d₆) δ: 11.78 (2H, br. s), 8.32 (1H, s), 7.41-7.31 (2H, m), 7.07-6.98 (3H, m), 6.00 (1H, d, J=5.8 Hz), 5.37 (1H, s), 5.18 (1H, s), 4.88 (2H, s), 4.85-4.78 (2H, m), 4.72-4.59 (3H, m), 4.34 (1H, m), 4.00 (1H, m), 3.75-3.56 (3H, m), 2.79-2.69 (2H, m).

[3] Synthesis of N²-phenoxyacetyl-5'-O-(4,4'-dimethoxytrityl)-2'-O-(2-cyanoethoxymethoxymethyl)guanosine (3d)

N²-phenoxyacetyl-2'-O-(2-cyanoethoxymethoxymethyl) guanosine (3c) (630 mg, 1.2 mmol)) was azeotropically distilled with pyridine, and dried in vacuo. The residue was dissolved in pyridine (6.0 mL), 4,4'-dimethoxytrityl chloride (600 mg, 1.8 mmol) was added at 0° C. and the mixture was stirred at room temperature for 2 hr. After completion of the reaction, methanol was added and the mixture was stirred for 10 min, and the solvent was evaporated under reduced pressure. To the residue was added dichloromethane and the mixture was washed twice with saturated aqueous sodium hydrogen carbonate solution and once with saturated aqueous sodium chloride solution. The organic layer after washing was dried over anhydrous sodium sulfate and concentrated under reduced pressure. The obtained crude product was purified by silica gel column chromatography (dichloromethane:ethyl acetate=1:1, containing 0.05% pyridine) to give the object compound (3d) (800 mg, purity 99.0%, yield 80%). The instrumental analytical values of compound (3d) are shown below.

Compound (3d):

$^1$H-NMR (400 MHz, CDCl$_3$) δ: 11.82 (1H, s), 8.63 (1H, s), 7.84 (1H, s), 7.43-7.21 (9H, m), 6.86-6.82 (4H, m), 6.06 (1H, d, J=5.9 Hz), 4.95 (1H, t, J=5.7 Hz), 4.78 (2H, m), 4.67-4.63 (2H, m), 4.50-4.45 (1H, m), 4.30-4.26 (1H, m), 3.81 (6H, s), 3.79-3.67 (2H, m), 3.44 (2H, dd, J=10.6, 3.7 Hz), 2.91 (1H, s), 2.64-2.56 (2H, m), 1.66 (3H, s).

[4] Synthesis of N$^2$-phenoxyacetyl-5'-O-(4,4'-dimethoxytrityl)-2'-O-(2-cyanoethoxymethoxymethyl)guanosine 3'-O-(2-cyanoethyl N,N-diisopropylphosphoramidite) (I-3)

N$^2$-phenoxyacetyl-5'-O-(4,4'-dimethoxytrityl)-2'-O-(2-cyanoethoxymethoxymethyl)guanosine (3d) (800 mg, 0.96 mmol) was azeotropically distilled with acetonitrile, and dried in vacuo. This operation was performed twice. To the thus-obtained mixture were added diisopropylammoniumtetrazolide (180 mg, 1.1 mmol) and acetonitrile (3 mL) under an argon atmosphere, 2-cyanoethyl-N,N,N',N'-tetraisopropylphosphordiamidite (0.61 mL, 1.9 mmol) was further added and the mixture was stirred at room temperature for 18 hr. After completion of the reaction, the solvent was evaporated under reduced pressure, ethyl acetate was added and the mixture was washed once with saturated aqueous sodium hydrogen carbonate solution and once with saturated aqueous sodium chloride solution. The organic layer after washing was dried over anhydrous sodium sulfate and concentrated under reduced pressure. The obtained crude product was purified by silica gel column chromatography (hexane:ethyl acetate=1:10, containing 0.1% triethylamine) to give the object compound (I-3) (803 mg, purity 98.3%, yield 81%). The instrumental analytical values of compound (I-3) are shown below.

Compound (I-3):

$^{31}$P-NMR (162 MHz, CDCl$_3$) δ: 152.7, 152.6.

Example 4

Synthesis of Adenosine EMM Amidite (I-4)

Adenosine EMM amidite (I-4) was synthesized according to the following scheme.

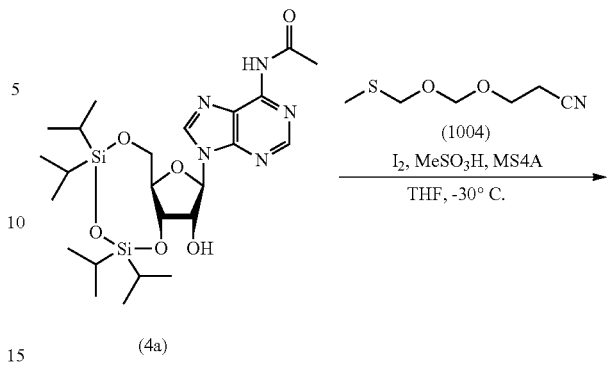

(4a)

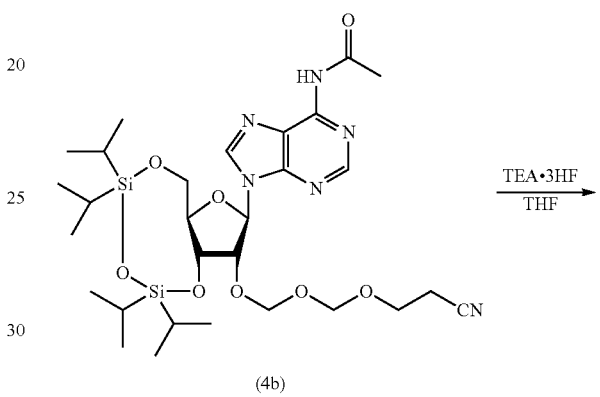

(4b)

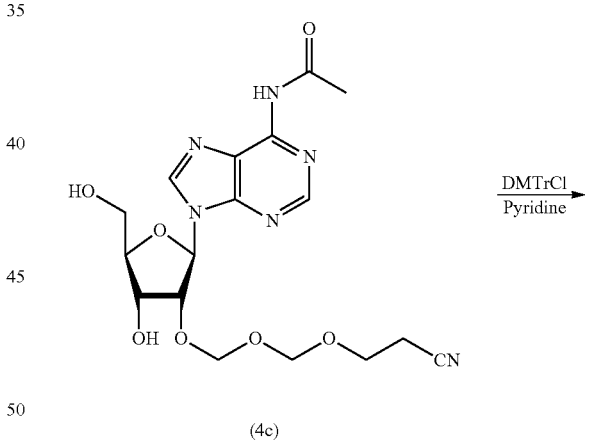

(4c)

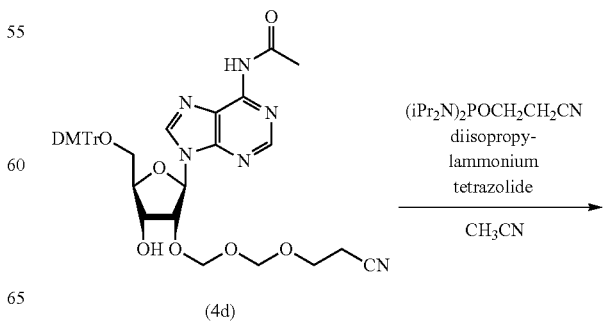

(4d)

-continued

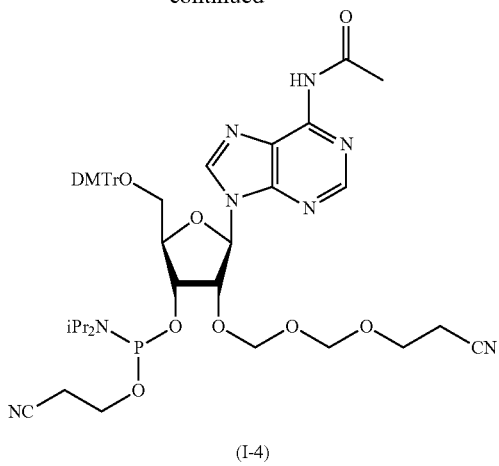

(I-4)

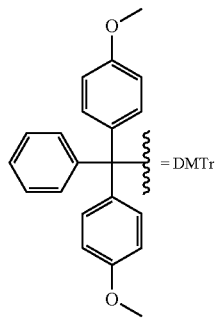 = DMTr

[1] Synthesis of N⁶-acetyl-3',5'-O-(tetraisopropyldisiloxane-1,3-diyl)-2'-O-(2-cyanoethoxymethoxymethyl)adenosine (4b)

Commercially available N⁶-acetyl-3',5'-O-(tetraisopropyldisiloxane-1,3-diyl)adenosine (4a) (1.0 g, 1.8 mmol) was azeotropically distilled twice with toluene and once with tetrahydrofuran, and dried in vacuo. Under an argon atmosphere, the dried product was dissolved in tetrahydrofuran (1.8 mL), molecular sieves 4A (1.0 g) was added, and the mixture was stirred at −30° C. for 10 min. Methanesulfonic acid (0.26 g, 2.7 mmol) was added at −30° C. and the mixture was stirred for 10 min. 2-Cyanoethoxymethylmethylthiomethylether (1004) (580 mg, 3.6 mmol) was added at −30° C. and the mixture was stirred for 10 min. Iodine (2.76 g, 10.9 mmol) was added and the mixture was stirred at −30° C. for 30 min. After completion of the reaction, to the reaction solution was added a cooled mixed solution of aqueous saturated sodium thiosulfate solution and saturated aqueous sodium hydrogen carbonate solution. The mixture was vigorously stirred until the brown color disappeared. The mixture was extracted with ethyl acetate, and the organic layer was washed twice with saturated aqueous sodium thiosulfate solution, once with saturated aqueous sodium hydrogen carbonate solution, and once with saturated aqueous sodium chloride solution. The organic layer after washing was dried over anhydrous sodium sulfate, and concentrated under reduced pressure to give the object compound (4b) as a crude product (1.32 g, purity 83.8%). The instrumental analytical values of the compound (4b) are shown below.

Compound (4b):
¹H-NMR (400 MHz, CDCl₃) δ: 8.68 (1H, s), 8.66 (1H, s), 8.33 (1H, s), 6.12 (1H, s), 5.08 (1H, d, J=7.0 Hz), 4.91-4.80 (3H, m), 4.67 (1H, d, J=7.8 Hz), 4.52 (1H, d, J=4.3 Hz), 4.25 (1H, d, J=13.0 Hz), 4.17 (1H, d, J=9.4 Hz), 4.09-4.02 (2H, m), 3.89-3.80 (1H, m), 2.67 (2H, m), 2.63 (3H, s), 1.11-0.98 (28H, m).

[2] Synthesis of N⁶-acetyl-2'-O-(2-cyanoethoxymethoxymethyl)adenosine (4c)

N⁶-acetyl-3',5'-O-(tetraisopropyldisiloxane-, 3-diyl)-2'-O-(2-cyanoethoxymethoxymethyl)adenosine (4b) (1.32 g, 2.0 mmol) was dissolved in tetrahydrofuran (6.0 mL) under an argon atmosphere. To the solution was added triethylamine trihydrofluoride (0.39 mL, 2.4 mmol), and the mixture was stirred at room temperature for 2 hr. Diisopropylether was added and the mixture was triturated, and the solvent was removed by decantation. This operation was performed 3 times. The obtained yellow solid-syrup-like substance was dried in vacuo to give the object compound (4c) (1.07 g). The instrumental analytical values of compound (4c) are shown below.

Compound (4c):
¹H-NMR (400 MHz, DMSO-d₆) δ: 10.71 (1H, s), 8.71 (1H, s), 8.66 (1H, s), 6.17 (1H, d, J=5.8 Hz), 5.41 (1H, d, J=5.4 Hz), 5.20 (2H, m), 4.80-4.73 (3H, m), 4.65-4.60 (2H, m), 4.37-4.33 (1H, m), 4.00-4.01 (1H, m), 3.73-3.64 (1H, m), 3.61-3.51 (2H, m), 2.79-2.64 (2H, m), 2.22 (3H, s).

[3] Synthesis of N⁶-acetyl-5'-O-(4,4'-dimethoxytrityl)-2'-O-(2-cyanoethoxymethoxymethyl)adenosine (4d)

N⁶-acetyl-2'-O-(2-cyanoethoxymethoxymethyl)adenosine (4c) (1.07 g, 2.5 mmol) was azeotropically distilled with pyridine, and dried in vacuo. The residue was dissolved in pyridine (10 mL), 4,4'-dimethoxytrityl chloride (1.2 g, 3.5 mmol) was added at 0° C. and the mixture was stirred at room temperature for 3 hr. After completion of the reaction, methanol was added and the mixture was stirred for 10 min, and the solvent was evaporated under reduced pressure. To the residue was added ethyl acetate and the mixture was washed twice with saturated aqueous sodium hydrogen carbonate solution and once with saturated aqueous sodium chloride solution. The organic layer after washing was dried over anhydrous sodium sulfate and concentrated under reduced pressure. The obtained crude product was purified by silica gel column chromatography (ethyl acetate, containing 0.05% pyridine) to give the object compound (4d) (670 mg, purity 99.6%). The instrumental analytical values of compound (4d) are shown below.

Compound (4d):
¹H-NMR (400 MHz, CDCl₃) δ: 8.62-8.58 (2H, m), 8.17 (1H, s), 7.46-7.39 (2H, m), 7.37-7.20 (7H, m), 6.87-6.79 (4H, m), 6.20 (1H, d, J=4.9 Hz), 5.03-4.75 (3H, m), 4.52 (1H, s), 4.30-4.23 (1H, m), 4.12 (2H, d, J=7.3 Hz), 3.79 (6H, s), 3.79-3.69 (2H, m), 3.52-3.44 (2H, m), 2.61 (3H, s), 2.58 (1H, d, J=5.5 Hz), 2.51 (2H, t, J=5.9 Hz).

[4] Synthesis of N⁶-acetyl-5'-O-(4,4'-dimethoxytrityl)-2'-O-(2-cyanoethoxymethoxymethyl)adenosine 3'-O-(2-cyanoethyl N,N-diisopropylphosphoramidite) (I-4)

N⁶-acetyl-5'-O-(4,4'-dimethoxytrityl)-2'-O-(2-cyanoethoxymethoxymethyl)adenosine (4d) (670 mg, 0.9 mmol) was azeotropically distilled with acetonitrile, and dried in vacuo. This operation was performed twice. Under an argon atmosphere, diisopropylammoniumtetrazolide (170 mg, 1.0 mmol) and acetonitrile (5.5 mL) were added, 2-cyanoethyl-N,N,N',N'-tetraisopropylphosphordiamidite (0.32 mL, 1.0 mmol) was further added, and the mixture was stirred at 40° C. for 3 hr. After completion of the reaction, the solvent was evaporated under reduced pressure. Ethyl acetate was added and the mixture was washed once with saturated aqueous sodium hydrogen carbonate solution and once with saturated aqueous sodium chloride solution. The organic layer after washing was dried over anhydrous sodium sulfate and concentrated under reduced pressure. The obtained crude product was purified by silica gel column chromatography (ethyl acetate:acetone=10:1, containing 0.1% triethylamine) to give the object compound (I-4) (700 mg, purity 98.3%, yield 82%). The instrumental analytical values of compound (I-4) are shown below.

Compound (I-4):

$^{31}$P-NMR (162 MHz, CDCl$_3$) δ: 152.7, 152.6.

INDUSTRIAL APPLICABILITY

According to the present invention, phosphoramidite to be a starting material of nucleic acid synthesis can be produced efficiently at a high purity. Along therewith, nucleic acid can be produced at a high purity in a high yield.

This application is based on a patent application No. 2015-076170 filed in Japan (filing date: Apr. 2, 2015) and a patent application No. 2015-122009 filed in Japan (filing date: Jun. 17, 2015), the contents of which are incorporated in full herein.

The invention claimed is:

1. A method of producing a glycoside compound represented by the formula (I):

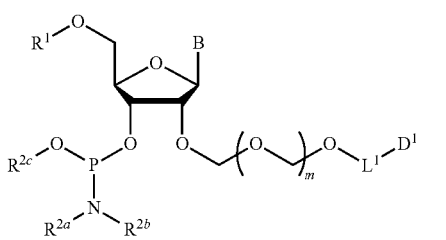
(I)

wherein R$^1$ is a hydroxyl-protecting group; R$^{2a}$ and R$^{2b}$ are the same or different and each is a hydrogen atom or a substituent; R$^{2c}$ is a hydrogen atom, an electron-withdrawing group or a substituent optionally substituted by an electron-withdrawing group; R$^{2a}$ and R$^{2b}$ optionally form a ring together with a nitrogen atom bonded thereto; B is an atomic group having a nucleic acid base skeleton; L$^1$ is an alkylene group; D$^1$ is an electron-withdrawing group; and m is a positive integer, or a salt thereof, comprising
a step of subjecting
a thioether compound represented by the formula (103):

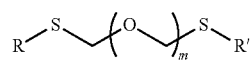
(103)

wherein m is as defined above; and R and R' are the same or different and each is an alkyl group, an alkenyl group, an alkynyl group, an aryl group, an aralkyl group, a cycloalkyl group, a cycloalkenyl group, a cycloalkylalkyl group, a cycloalkenylalkyl group or an alkoxyalkyl group, and an alcohol compound represented by the formula (105):

(105)

wherein each symbol is as defined above,
to a coupling reaction in the presence of a halogenating agent, a desiccant and a Lewis acid, and then to distillation in the presence of at least one maleimide group-containing compound to give a thioether compound represented by the formula (104):

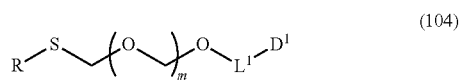
(104)

wherein each symbol is as defined above (Step 0); and
a step of subjecting a glycoside compound represented by the formula (Ia):

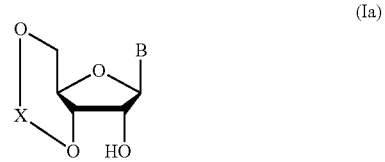
(Ia)

wherein B is as defined above; and X is a group represented by the following formula:

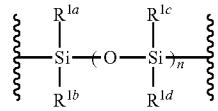

wherein n is 0 or 1; and R$^{1a}$-R$^{1d}$ are the same or different and each is a hydrogen atom, an alkyl group or an alkoxy group, and a thioether compound represented by the formula (104)
to a coupling reaction in the presence of a halogenating agent, a desiccant and a Lewis acid to give a glycoside compound represented by the formula (Ib):

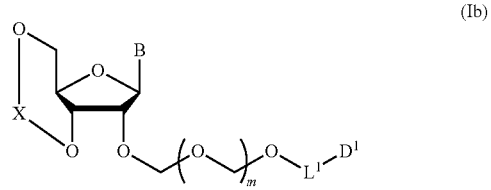
(Ib)

wherein each symbol is as defined above (Step 1).

2. The production method according to claim 1, further comprising a step of deprotecting the compound represented by the formula (Ib) to give a glycoside compound represented by the formula (Ic):

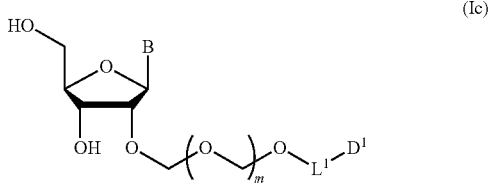

(Ic)

wherein each symbol is as defined in claim 1 (Step 2).

3. The production method according to claim 2, further comprising a step of introducing a hydroxyl-protecting group into the glycoside compound represented by the formula (Ic) to give a glycoside compound represented by the formula (Id):

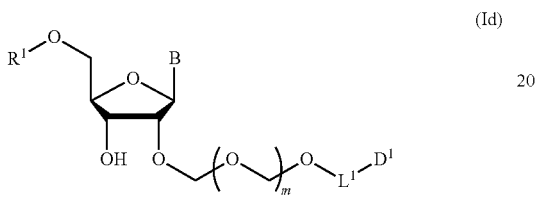

(Id)

wherein each symbol is as defined in claim 1 (Step 3).

4. The production method according to claim 3, further comprising a step of phosphorylating the glycoside compound represented by the formula (Id) to give glycoside compound represented by the formula (I) (Step 4).

5. A method of producing a glycoside compound represented by the formula (Ib):

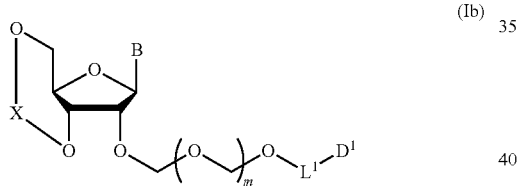

(Ib)

wherein B is an atomic group having a nucleic acid base skeleton; $L^1$ is an alkylene group; $D^1$ is an electron-withdrawing group; and m is a positive integer, comprising
a step of subjecting
a thioether compound represented by the formula (103):

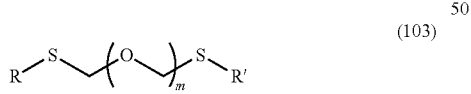

(103)

wherein m is as defined above; and R and R' are the same or different and each is an alkyl group, an alkenyl group, an alkynyl group, an aryl group, an aralkyl group, a cycloalkyl group, a cycloalkenyl group, a cycloalkylalkyl group, a cycloalkenylalkyl group or an alkoxyalkyl group, and
an alcohol compound represented by the formula (105):

(105)

wherein each symbol is as defined above, to a coupling reaction in the presence of a halogenating agent, a desiccant and a Lewis acid, and then to distillation in the presence of at least one maleimide group-containing compound to give a thioether compound represented by the formula (104):

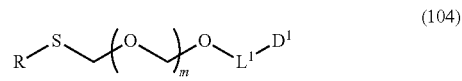

(104)

wherein each symbol is as defined above (Step 0); and
a step of subjecting a glycoside compound represented by the formula (Ia):

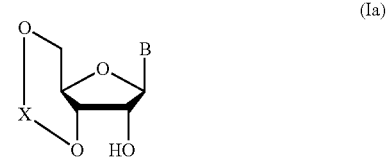

(Ia)

wherein B is as defined above; and X is a group represented by the following formula:

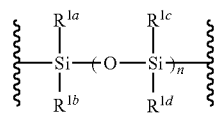

wherein n is 0 or 1; and $R^{1a}$-$R^{1d}$ are the same or different and each is a hydrogen atom, an alkyl group or an alkoxy group, and a thioether compound represented by the formula (104)
to a coupling reaction in the presence of a halogenating agent, a desiccant and a Lewis acid (Step 1).

6. A method of producing a glycoside compound represented by the formula (Ic):

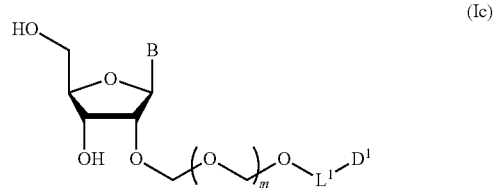

(Ic)

wherein B is an atomic group having a nucleic acid base skeleton; $L^1$ is an alkylene group; $D^1$ is an electron-withdrawing group; and m is a positive integer, comprising
a step of subjecting a thioether compound represented by the formula (103):

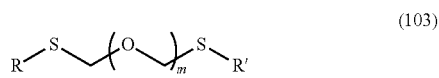

(103)

wherein m is as defined above; and R and R' are the same or different and each is an alkyl group, an alkenyl group, an alkynyl group, an aryl group, an aralkyl group, a cycloalkyl group, a cycloalkenyl group, a cycloalkylalkyl group, a cycloalkenylalkyl group or an alkoxyalkyl group, and an alcohol compound represented by the formula (105):

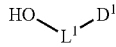
(105)

wherein each symbol is as defined above,
to a coupling reaction in the presence of a halogenating agent, a desiccant and a Lewis acid, and then to distillation in the presence of at least one maleimide group-containing compound to give a thioether compound represented by the formula (104):

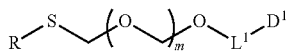
(104)

wherein each symbol is as defined above (Step 0); and
a step of subjecting a glycoside compound represented by the formula (Ia):

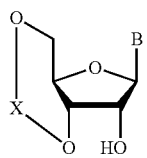
(Ia)

wherein B is as defined above; and X is a group represented by the following formula:

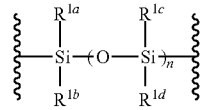

wherein n is 0 or 1; and $R^{1a}$-$R^{1d}$ are the same or different and each is a hydrogen atom, an alkyl group or an alkoxy group, and a thioether compound represented by the formula (104)
to a coupling reaction in the presence of a halogenating agent, a desiccant and a Lewis acid to give a glycoside compound represented by the formula (Ib):

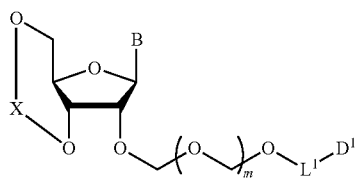
(Ib)

wherein each symbol is as defined above (Step 1); and
a step of deprotecting the glycoside compound represented by the formula (Ib) (Step 2).

7. A method of producing a glycoside compound represented by the formula (Id):

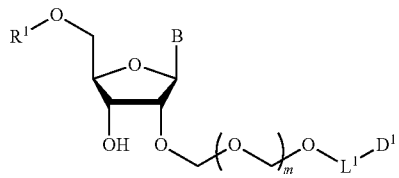
(Id)

wherein $R^1$ is a hydroxyl-protecting group; B is an atomic group having a nucleic acid base skeleton; $L^1$ is an alkylene group; $D^1$ is an electron-withdrawing group; and m is a positive integer, comprising
a step of subjecting a thioether compound represented by the formula (103):

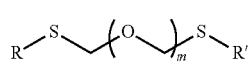
(103)

wherein m is as defined above; and R and R' are the same or different and each is an alkyl group, an alkenyl group, an alkynyl group, an aryl group, an aralkyl group, a cycloalkyl group, a cycloalkenyl group, a cycloalkylalkyl group, a cycloalkenylalkyl group or an alkoxyalkyl group, and an alcohol compound represented by the formula (105):

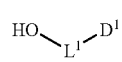
(105)

wherein each symbol is as defined above,
to a coupling reaction in the presence of a halogenating agent, a desiccant and a Lewis acid, and then to distillation in the presence of at least one maleimide group-containing compound to give a thioether compound represented by the formula (104):

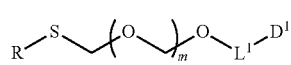
(104)

wherein each symbol is as defined above (Step 0); and
a step of subjecting a glycoside compound represented by the formula (Ia):

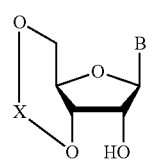
(Ia)

wherein B is as defined above; and X is a group represented by the following formula:

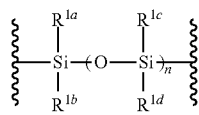

wherein n is 0 or 1; and $R^{1a}$-$R^{1d}$ are the same or different and each is a hydrogen atom, an alkyl group or an alkoxy group, and a thioether compound represented by the formula (104)

to a coupling reaction in the presence of a halogenating agent, a desiccant and a Lewis acid to give a glycoside compound represented by the formula (Ib):

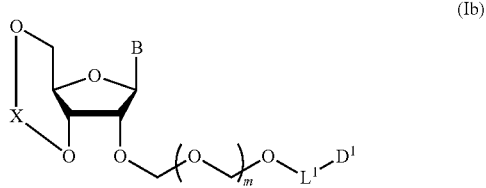

wherein each symbol is as defined above (Step 1);

a step of deprotecting the glycoside compound represented by the formula (Ib) to give a glycoside compound represented by the formula (Ic):

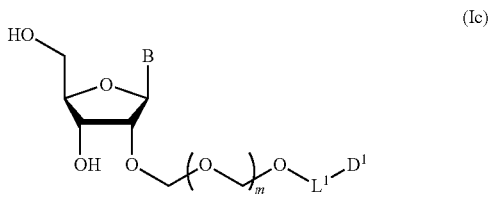

wherein each symbol is as defined above (Step 2); and a step of introducing a hydroxyl-protecting group into the glycoside compound represented by the formula (Ic) (Step 3).

8. The method according to claim 1, wherein the maleimide group-containing compound in the distillation in Step 0 is 4,4'-bismaleimidodiphenylmethane.

9. The method according to claim 1, wherein n is 1.

10. The method according to claim 1, wherein $R^{1a}$-$R^{1d}$ are isopropyl groups.

11. The method according to claim 1, wherein m is 1.

12. The method according to claim 1, wherein $L^1$ is an ethylene group.

13. The method according to claim 1, wherein $D^1$ is a cyano group.

14. The method according to claim 1, wherein the thioether compound represented by the formula (104) is added after the addition of the halogenating agent, the desiccant and the Lewis acid in Step 1.

15. The method according to claim 1, wherein the halogenating agent is added after the addition of the desiccant, the Lewis acid and the thioether compound represented by the formula (104) in Step 1.

16. The method according to claim 14, wherein the Lewis acid is added after the addition of the halogenating agent in Step 1.

17. The method according to claim 15, wherein the thioether compound represented by the formula (104) is added after the addition of the Lewis acid in Step 1.

18. The method according to claim 1, wherein the halogenating agent in Step 1 is an iodinating agent.

19. The method according to claim 18, wherein the iodinating agent is 1,3-diiodo-5,5-dimethylhydantoin or iodine.

20. The method according to claim 1, wherein the Lewis acid in Step 1 is trifluoromethanesulfonic acid or methanesulfonic acid.

* * * * *